Figure 1A:
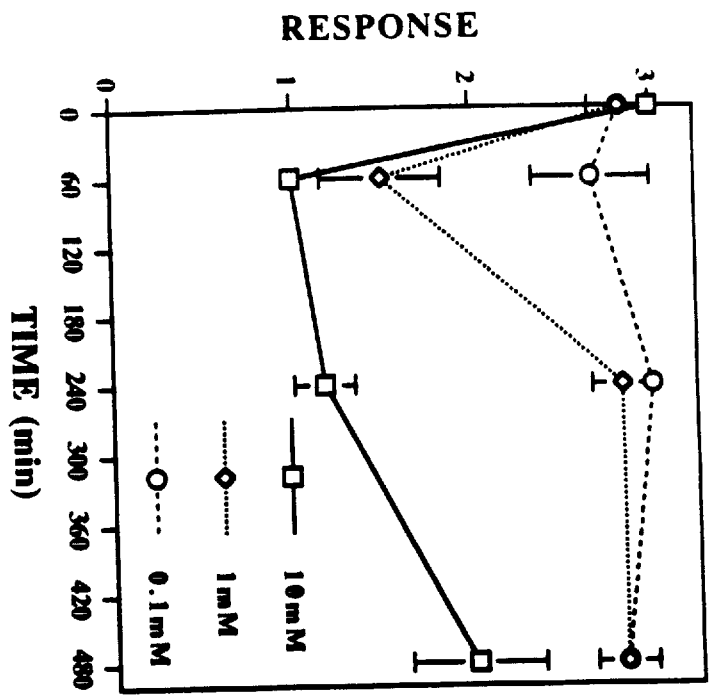

US006030974A

United States Patent [19]
Schwartz et al.

[11] Patent Number: 6,030,974
[45] Date of Patent: Feb. 29, 2000

[54] METHOD OF ANESTHESIA

[75] Inventors: Daniel M. Schwartz, San Francisco; Howard L. Fields, Berkeley, both of Calif.

[73] Assignee: The Regents of the University of California, Oakland, Calif.

[21] Appl. No.: 09/054,800

[22] Filed: Apr. 2, 1998

Related U.S. Application Data

[60] Provisional application No. 60/076,317, Feb. 27, 1998, and provisional application No. 60/040,903, Apr. 2, 1997.

[51] Int. Cl.$^7$ .................................................. A61K 31/505
[52] U.S. Cl. ........................ 514/267; 514/817; 514/818; 514/912
[58] Field of Search ................................... 514/267, 817, 514/818, 912

[56] References Cited

U.S. PATENT DOCUMENTS

| | | |
|---|---|---|
| 3,892,847 | 7/1975 | Adams et al. . |
| 3,898,339 | 8/1975 | Adams et al. ........................... 424/251 |
| 3,966,934 | 6/1976 | Adams et al. . |
| 4,022,899 | 5/1977 | Adams et al. . |
| 5,506,257 | 4/1996 | MacLeod et al. ....................... 514/422 |

FOREIGN PATENT DOCUMENTS

| | | | |
|---|---|---|---|
| 983850 | 2/1976 | Canada .................................. 167/100 |
| 986012 | 3/1976 | Canada .................................. 167/100 |
| 21 63 055 | 12/1972 | Germany . |
| 55-94319 | 7/1970 | Japan .............................. A61K 27/00 |

OTHER PUBLICATIONS

CA 69:9494, Ogura et al., 1968.
CA 85:116725, Adams et al., 1976.
CA 86:115142, Adams et al., 1976.
********, Tetrodotoxin Poisoning Associated With Eating Puffer Fish Transported from Japan–California, 1996, The Morbidity and Mortality Weekly Report, vol. 45, No. 19, May 17, 1996.
Adams, Arch. Int. Pharmacodyn. Ther. (1976) 224(2), 275–82, Abstract XP002075603.
Adams, The Local Anesthetic Activity of Tetrodotoxin Alone and in Combination With Vasoconstrictors and Local Anesthetics, Anasthesia and Analgesia . . . Current Researches, vol. 55, No. 4, Jul.–Aug. 1976.
Attia, Effect of Local Anesthesia and Ocular Message on Central Corneal Curvature, Ann. Ophthalmol., vol. 22, No. 10, pp. 395–398, Oct. 1990.
Bower, Nonprotein Neurotoxins, Clinical Toxicology, vol. 18, No. 7, pp. 813–863, 1981.
Butterworth, Molecular Mechanisms of Local Anesthesia: A Review, Anesthesiology, vol. 72, No. 4, pp. 711–734, Apr. 1990.
Bynke, Is Substance P Necessary for Corneal Nociception?, European Journal of Pharmacology, vol. 101, pp. 253–258, 1984.
Catterall, Chapter 15 Local Anesthetics, Goodman & Gilman's The Pharmacological basis of Therapeutics, Ninth Edition, pp. 331–347, 1996, McGraw–Hill.

Cherry, The Treatment of Pain Following Excimer Laser Photorefractive Keratectomy: Additive Effect of Local Anesthetic Drops, Topical Diclofenac, and Bandage Soft Contact, Supplement to Ophthalmic Surgery and Lasers, vol. 27, No. 5, pp. S477–S480, May 1996.
Chrai, Drop Size and Initial Dosing Frequency Problems of Topically Applied Ophthalmic Drugs, Journal of Pharmaceutical Sciences, vol. 63, No. 3, pp. 333–338, Mar. 1974.
Cornish, Susceptibility of Man to Pufferfish Toxin, The Medical Journal of Australia, pp. 48, Jul. 7, 1973.
Epstein, Keratitis from Misuse of Corneal Anesthetics, The New England Journal of Medicine, vol. 279, No. 8, pp. 396–399, Aug. 22, 1968.
Evans, Tetrodotoxin, Saxitoxin, and Related Substances: Their Applications in Neurobiology, International Review of Neurobiology, vol. 15, pp. 83–166, 1972, Academic Press.
Gallar, Irritation of the Anterior Segment of the Eye by Ultraviolet Radiation: Influence of Nerve Blockade and calcium Antagonists, Current Eye Research (1995), pp. 828–835, Oxford University Press.
Goto, Tetrodotoxin, Tetrahedron, vol. 21, pp. 2059–2088, 1965.
Grant, Comparative Toxicity of Tetracaine, Proparacaine and Cocaine Evaluated with Primary Cultures of Rabbit Corneal Epithelial Cells, Exp. Eye Res., vol. 58, pp. 469–478, 1994.
Hamasaki, A Biological Method for the Quantitative Measurement of Tetrodotoxin (TTX) : Tissue Culture Bioassay in Combination with a Water–Soluble Tetrazolium Salt, Toxicon, vol. 34, No. 4, pp. 490–495, 1996.
Horsburgh, Chemical Properties and Physiological Actions of Triturus Embryonic Toxin, The Journal of Pharmacology and Experimental Therapeutics, vol. 68, pp. 284–291, 1940.
Ishihara, Uber die physiologischen Wirkungen des Fugutoxins, Mitteilungen aus der Medizinischen Fakultat der Kaiserlichen Universitat zu Tokyo, 1918, pp. 376–426.
Josephson, Corneal Staining After Instillation of Topical Anesthetic, Investigative Ophthalmology & Visual Science, vol. 29, No. 7, pp. 1096–1099, Jul. 1988.
Kao, Pharmacological Studies on Tarichatoxin, a Potent Neurotoxin, The Journal of Pharmacology and Experimental Therapeutics, vol. 140, No. 1, pp. 31–39, Apr. 1963.
Kao, Tetrodotoxin, Saxitoxin and Their Significance in the Study of Excitation Phenomena, Pharmacological Review, vol. 18, No. 2, pp. 997–1049, 1966, The Williams & Wilkins Co.

(List continued on next page.)

*Primary Examiner*—Kimberly Jordan
*Attorney, Agent, or Firm*—Cooley Godward LLP

[57] ABSTRACT

A method of producing local anesthesia in a mammal experiencing pain in an epithelial tissue region is described. The method includes topically administering to the region, in a suitable pharmaceutical vehicle, an effective dose of a long-acting sodium channel blocking compound.

38 Claims, 10 Drawing Sheets

OTHER PUBLICATIONS

Kishi, Synthetic Approach Towards Tetrodotoxin—A Stereospecific Synthesis of a Compund Having the Same Six Chiral Centers on the Cyclohexane Ring as those of Tetrodotoxin, Tetrahedron Letters, No. 59, pp. 5129–5132, 1970.

Lange, Pufferfish Poisoning, AFP, vol. 42, No. 4, pp. 1029–1033, Oct. 1994.

Lee, Review: Topical Ocular Drug Delivery: Recent Developments and Future Challenges, Journal of Ocular Pharmacology, vol. 2, No. 1, pp. 67–108, 1986, Mary Ann Liebert, Inc., Publishers.

Lim–Bon–Siong, Efficacy and Safety of the ProTek (Vifilcon A) Therapeutic Soft Contact Lens After Photorefractive Keratectomy, American Journal of Ophthalmology, vol. 125, No. 2, pp. 169–176, 1998.

Manger, Tetrazolium–Based Cell Bioassay for Neurotoxins Active on Voltage–Sensitive Sodium Channels: Semiautomated Assay for Saxitoxins, Brevetoxins and Ciguatoxins, Analytical biochemistry, vol. 214, pp. 190–194, 1993.

Maurice, The Absence of Corneal Toxicity With Low–Level Topical Anesthesia, American Journal of Ophthalmology, vol. 99, pp. 691–696, Jun. 1985.

Mills, Occasional Survey—Pelagic Paralysis, The Lancet, pp. 161–164, Jan. 23, 1998.

Mosher, Tarichatoxin—Tetrodotoxin: A Potent Neurotoxin, Science, vol. 144, pp. 1100–1110, May 29, 1964.

Ogura, Mechanism of Local Anesthetic Action of Crystalline Tetrodotoxin and Its Derivatives, European Journal of Pharmacology 3 (1968), pp. 58–67, North–Holland Publ. Comp., Amsterdam.

Peyman, Effects of Morphine on Corneal Sensitivity and Epithelial Wound Healing: Implications for Topical Ophthalmic Analgesia, British Journal of Ophthalmology, vol. 78, pp. 138–141, 1994.

Ramselaar, Corneal Epithelial Permeability After Instillation of Ophthalmic Solutions Containing Local Anaesthetics and Preservatives, Current Eye Research, vol. 7, No. 9, 1988.

Raybould, A Monoclonal Antibody–Based Immunoassay for Detecting Tetrodotoxin in Biological Samples, Jounrnal of Clinical Laboratory Analysis, vol. 6, pp. 65–72, 1992.

Ritchie, Tetrodotoxin and Saxitoxin, and the Sodium Channels of Excitable Tissue, TIPS, pp. 275–279, Jun. 1980.

Rogers, Molecular Determinants of High Affinity Binding of – Scorpion Toxin and Sea Anemone Toxin in the S3–S4 Extracellular Loop in Domain IV of the $Na^+$ Channel Subunit, The Journal of Biological Chemistry, vol. 271, No. 27, Issue of Jul. 5, pp. 15950–15962, 1996.

Rosenwasser, Complications of Topical Ocular Anesthetics, International Ophthalmology Clinics, vol. 29, No. 3, pp. 153–158, Fall 1989.

Rosenwasser, Topical Anesthetic Abuse, Ophthalmology, vol. 97, No. 8, pp. 967–972, Aug. 1990.

Salminen, Review: Systemic Absorption of Topically Applied Ocular Drugs in Humans, Journal of Ocular Pharmacology, vol. 6, No. 3, pp. 243–249, 1990.

Schoenwald, Ocular Drug Delivery Pharmacokinetic Considerations, Clin. Pharmacokinet., vol. 18, No. 4, pp. 255–269, 1990.

Schwartz, Experimental Use of Tetrodoxin for Corneal Pain After Excimer Laser Keratectomy, Cornea, vol. 17, No. 2, pp. 196–199, 1998.

Sims, Pufferfish Poisoning: Emergency Diagnosis and Management of Mild Human Tetrodotoxication, Annals of emergency Medicine, vol. 15, pp. 149–153, Sep. 9, 1986.

Sklar, Topical Anesthesia of the Eye as a Diagnostic Test, Annals of Emergency Medicine, vol. 18, pp. 115–117, Nov. 11, 1989.

Smelser, Effect of Local Anesthetics of Cell Division and Migration Following Thermal Burns of Cornea, Archives of Ophthalmology, vol. 34, No. 4, pp. 271–277, Oct. 1945.

Terlau, Mapping the Site of Block By Tetrodotoxin and Saxitoxin of Sodium Channel II, FEBS Letters, vol. 293, Nos. 1–2, pp. 93–96, Nov. 1991.

Ulbricht, The Influence of pH on Equilibrium Effects of Tetrodotoxin on Myelinated Nerve Fibres of Rana Esculenta, J. Physiol., vol. 252, No. 1, pp. 159–184, 1975.

Unger, Prostaglandin and Neurogenically Mediated Ocular Response to Laser Irradiation of theRabbit Iris, Exp. Eye Res., vol. 25, pp. 209–220, 1977.

Weiss, The Effect of Corneal Hypesthesis on the Duration of Proparacaine Anesthetic Eyedrops, American Journal of Ophthalmology, vol. 112, No. 3, pp. 326–330, Sep. 1991.

Yagiela, Anesth. Prog. (1985) 32/2 (47–56), Abstract No. XP002075605.

Yasumoto, Fluorometric Determination of Tetrodotoxin by High Performance Liquid Chromatography, Agric. Biol. Chem., vol. 49, No. 10, pp. 3077–3080, 1985.

Yotsu, An Improved Tetrodotoxin Analyzer, Agric. Biol. Chem., vol. 53, No. 3, pp. 893–895, 1989.

Zhang, Hebei Yixueyuan Xuebao (1989) 10(1), 9–13, Abstract XP002075602.

Behrendt, T. American Journal of Ophthalmology 41:99–105 (1956).

Marr, WG et al., American Journal of Ophthalmology 43(4) Part 1, pp. 606–610 (1997).

Narahashi, T. et al., Neuroscience Research 4:65–99 (1971).

Smith RB. et al., International Ophthalmology Clinics 13(2):35–60 (1973).

Chapter 26, Toxic effects of Animal Toxins (citation could not be obtained) (1990).

Figure 7:
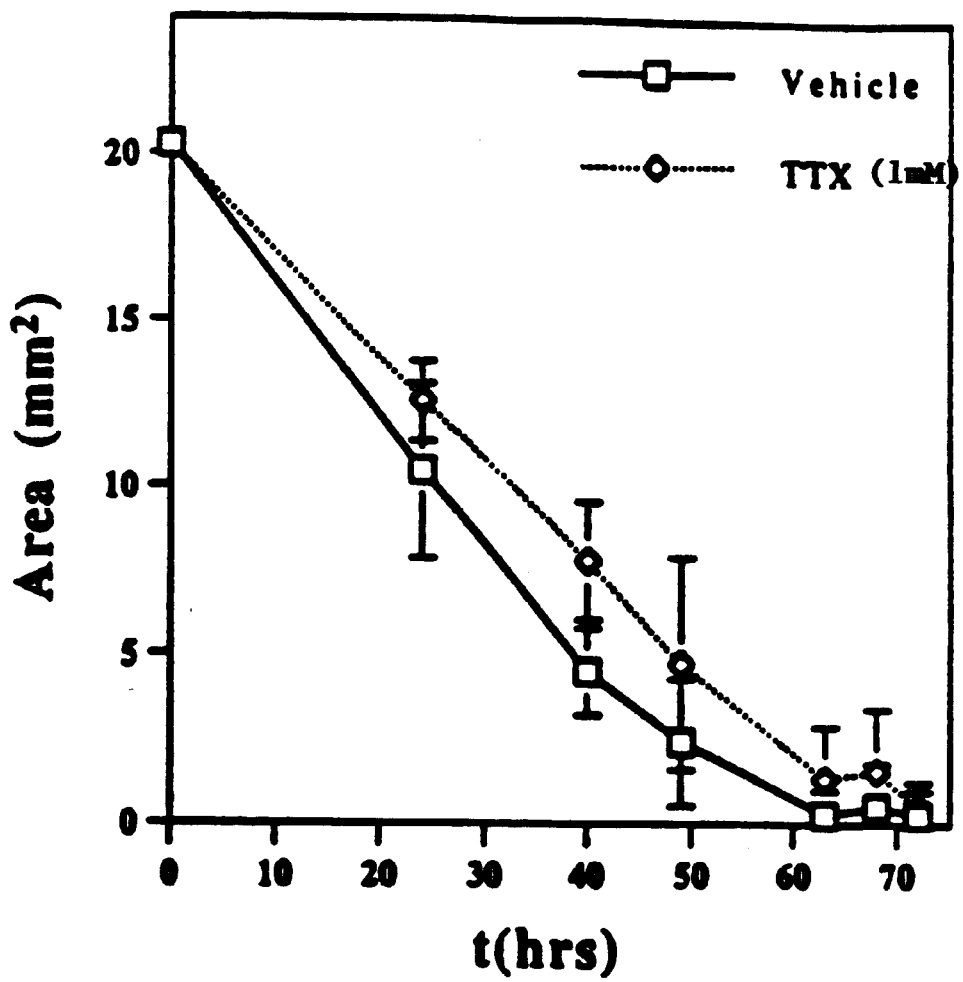
Figure 8:
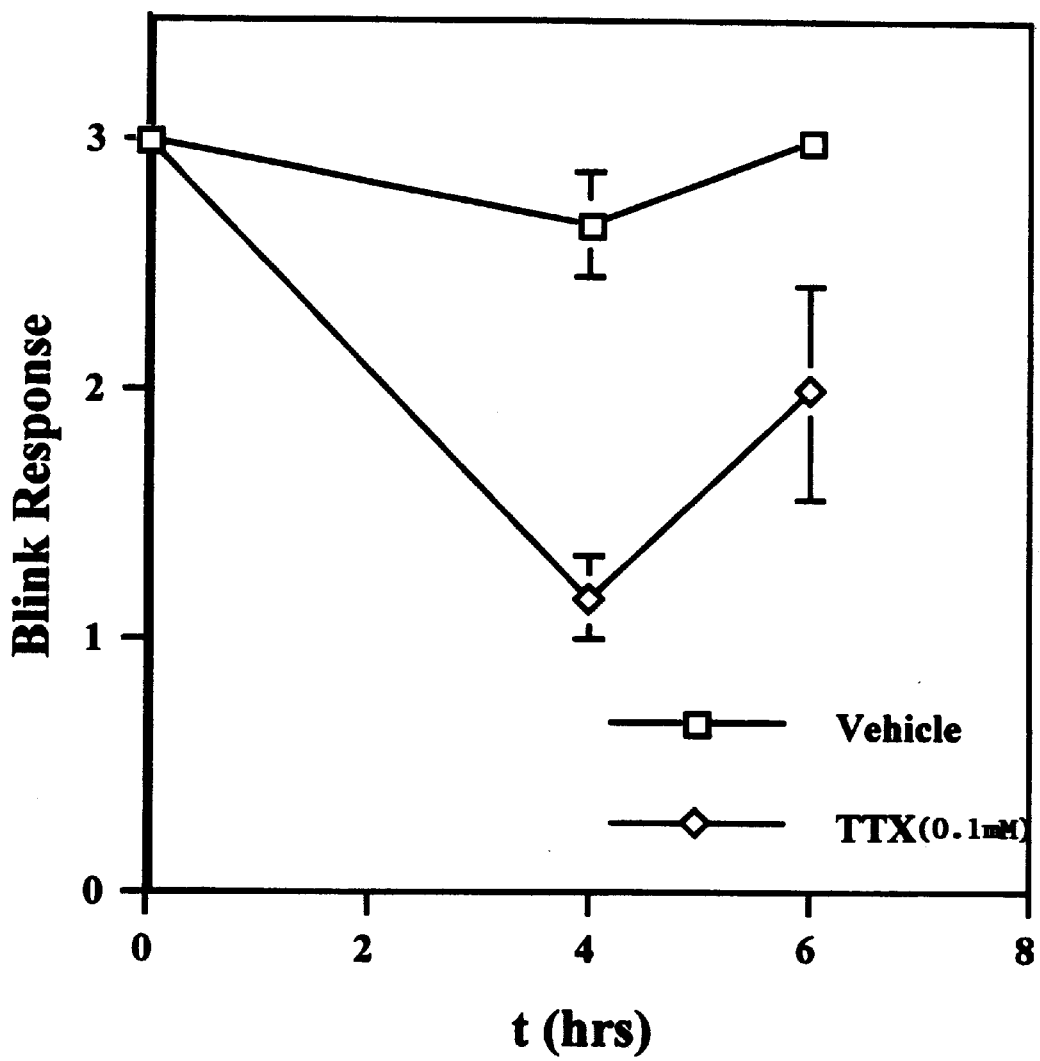

FIG. 7 Epithelial wound healing. Wound healing was assessed by measuring the size of the epithelial defect remaining at 24, 40, 49, 63, 68, and 72 h after excimer laser keratectomy. The results are given as the area of the epithelial defect remaining in 1 m$M$ TTX- or vehicle-treated eyes (mean±SD; $N$ = 6).

METHOD OF ANESTHESIA

CROSS REFERENCE TO RELATED APPLICATIONS

This application claims the benefit of U.S. Provisional Application No. 60/040,903, filed Apr. 2, 1997 and U.S. Provisional Application No. 60/076,317, filed Feb. 27, 1998.

FIELD OF THE INVENTION

The present invention relates to a method for producing local anesthesia by topical administration of sodium channel blocking compounds, including tetrodotoxin and saxitoxin.

BACKGROUND OF THE INVENTION

Pain is a well known phenomenon as an indicator of actual or potential injury or tissue damage due to inflammation, ischemia, mechanical or other irritation. Treatment of pain includes the use of local anesthetics, which block neuronal transmission and affect sensation as well as pain, and analgesics, which relieve pain and additionally may interfere with the activity of chemical mediators of inflammation.

Loss or damage of epithelial tissue is usually associated with moderate to severe pain and can result from a number of causes, for example, burns, corneal abrasions, other abnormalities of mucosal tissues, and surgical procedures involving epithelial and other tissues.

An example of pain associated with a surgical procedure is surgical correction of myopia by excimer laser photorefractive keratectomy. Following photorefractive keratectomy (PRK), patients generally experience moderate to severe eye pain in the first 24 to 48 hours. Current pain management with bandage contact lens, non-steroidal anti-inflammatory agents, and oral analgesics mitigates, but does not eliminate, the discomfort in most patients (Cherry, Tutton). Topical anesthetics have been used to reduce pain, but due to their short duration of action, frequent administration is required. For example, benoxinate, cocaine, tetracaine, and proparacaine are commonly prescribed topical anesthetics for management of eye pain. These topical anesthetics only provide pain relief for short periods, on the order of 15 to 30 minutes. Given frequently, these agents can be toxic to the corneal epithelium and inhibit re-epithelialization (Rosenwasser).

Thus, there is a need in the art for methods of producing long-lasting, local anesthesia without inhibiting re-epithelialization or healing of other tissues.

SUMMARY OF THE INVENTION

The methods and compositions of the present invention solve, inter alia, the long-recognized need in the art for methods of producing local anesthesia of long duration. In the particular embodiment of producing long-lasting local anesthesia of the corneal surface of an eye, the inventors have addressed a problem of great clinical significance, showing for the first time that sodium channel blocking compounds, such as tetrodotoxin and saxitoxin, can produce ocular surface anesthesia of long duration without impairing re-epithelialization. Moreover, the inventors have shown that the effective doses of those sodium channel blocking compounds have a wide margin of safety and that systemic absorption of tetrodotoxin topically administered to abraded corneas is low.

The methods and compositions of the invention can be used for any condition involving ocular surface pain, including local anesthesia following ocular surgery, including PRK, and following injury to the eye. The methods provide significant advantages, including providing at least 3 hours, preferably at least 4 hours, more preferably at least 6 hours, and most preferably, at least 8 hours of local anesthesia without affecting re-epithelialization of the corneal surface (e.g. wound healing).

The present invention includes methods of producing long-lasting local anesthesia, comprising administering a pharmaceutically acceptable composition of a long-acting sodium channel blocking compound, wherein said compound binds to the extracellular mouth of the sodium channel, occluding the channel by a mechanism separate from that of local anesthetics, such as proparacaine. Preferably, such methods achieve local anesthesia of long duration, lasting at least 3 hours (3 to 10 hours), preferably at least 4 hours (4–10 hours), and most preferably at least 6 to 10 hours. Preferred compounds include toxins or analogs thereof that specifically bind to a site formed in part by an extracellular region of the alpha subunit of a sodium channel. Most preferred compounds comprise the class of toxins and analogs that specifically bind to a site formed by the SS1 and SS2 extracellular regions of the alpha subunit of a sodium channel, wherein such compounds include tetrodotoxin, saxitoxin and analogs thereof. Surprisingly, these long-acting sodium channel blocking compounds, which are well known, potent neurotoxins, provide long-lasting local anesthesia without inhibiting reepithelialization.

Accordingly, it is an object of the invention to provide a method of producing local anesthesia in patients experiencing pain associated with damage to epithelial tissue.

It is another object of the invention to provide a method of producing local anesthesia for long-acting pain control.

It is another object of the invention to provide a method of producing local anesthesia in epithelial tissues having damage associated with corneal abrasions, as in, for example, ophthalmic surgery, such as post-operative photorefractive keratectomy, other forms of corneal refractive surgery, including excimer laser PRK and LASIK, without impairing healing of the epithelial tissue. Other applications include, but are not limited to, any condition where ocular surface anesthesia of long duration is desired, including after surgery or injury.

In one aspect, the invention includes a method of producing local anesthesia in a subject experiencing pain in an epithelial tissue region. The method includes topically administering to the region, in a suitable pharmaceutical vehicle, an effective dose of tetrodotoxin or saxitoxin.

In one embodiment, the effective dose of tetrodotoxin or saxitoxin is administered from a formulation containing tetrodotoxin or saxitoxin at a concentration of between 0.001 mM and 10 mM.

In another embodiment, tetrodotoxin or saxitoxin is administered to a de-epithelialized corneal tissue region. For example, tetrodotoxin is administered to the eye following excimer laser photorefractive keratectomy by instillation of drops. In this application, tetrodotoxin is typically formulated in a vehicle having a pH of between 4–8, more preferably between about 5–7.5.

In one embodiment, tetrodotoxin or saxitoxin is administered topically every 6–8 hours for between about 24–72 hours.

The method of the invention, in another embodiment, is for producing local anesthesia by topical administration of tetrodotoxin to an epithelial tissue region in the upper or lower gastrointestinal tract. In other embodiments, the epithelial tissue region is associated with genital lesions in the genital area, with epithelial tissue region is in the esophagus, or with facial epithelial tissue.

In another aspect, the invention includes a method of producing local anesthesia in the eye of a mammalian subject, by topically administering to the corneal surface of the eye of the subject, in a pharmaceutically suitable vehicle, a pharmaceutically effective dose of tetrodotoxin, saxitoxin or other long-acting sodium channel blocking compound. Such methods find application whenever ocular surface anesthesia is desired.

In one embodiment of this aspect, the corneal surface is partially or completely de-epithelialized.

In a third aspect, the invention includes a method of reducing pain following corneal surgery, including but not limited to excimer laser photorefractive keratectomy, by topically administering to the corneal surface of the eye of the subject, in a pharmaceutically suitable vehicle, a pharmaceutically effective dose of tetrodotoxin or saxitoxin.

In one embodiment of the third aspect, the method also includes the step of instilling drops of a non-steroidal anti-inflammatory compound in the eye of the subject. In other embodiments, the method further includes applying a bandage contact lens to the eye of the subject, or administering an antibiotic, steroid, or non-steroidal anti-inflammatory drug to the subject. Methods of administering combination drops to the eye are also contemplated, wherein such drops contain a composition comprising a long-acting sodium channel blocking compound and an antibiotic, steroid, or nonsteroidal anti-inflammatory drug in an opthalmically acceptable vehicle.

In yet another embodiment, the invention includes methods of producing local anesthesia in an eye of a mammal, comprising (a) topically administering to the corneal surface of the eye of said mammal, in a pharmaceutically suitable vehicle, 0.05%–0.5% proparacaine and (b) topically administering to the corneal surface of the eye of said mammal, in a pharmaceutically suitable vehicle, an opthalmically effective dose of a long-acting sodium channel blocking compound, wherein step (b) follows step (a). In a preferred embodiment, a 0.05% proparacaine concentration is administered.

Also provided are compositions of a long-acting sodium channel blocking compound in an opthalmically acceptable pH range of between 4–8, wherein the concentration of said compound is not greater than 1 mM (0.01 mM to 1 mM), preferably not greater than 0.5 mM (0.01 mM to 0.5 mM), more preferably not greater than 0.2 mM (0.01 mM to 0.2 mM), and most preferably not greater than 0.1 mM (0.01 mM to 0.1 mM).

These and other objects and features of the invention will be more fully appreciated when the following detailed description of the invention is read in conjunction with the accompanying drawings.

BRIEF DESCRIPTION OF THE DRAWINGS

FIG. 1A is a plot showing corneal blink response in rabbit eyes as a function of time after administration to the cornea with intact epithelium of 0.1 mM (open circles), 1 mM (open diamonds) and 10 mM (open squares) tetrodotoxin;

FIG. 1B is a plot showing corneal blink response in fellow rabbit eyes for FIG. 1A following topical administration of the vehicle only control;

FIG. 2A is a plot showing corneal blink response in rabbit eyes with intact corneal epithelium as a function of time following topical administration of 1 mM tetrodotoxin, 10 mM tetrodotoxin or a comparative anesthetic, 0.5% proparacaine;

FIG. 2B is a plot showing corneal blink response in fellow rabbit eyes for FIG. 2A following administration of the vehicle only control;

FIGS. 3A–3B are plots showing corneal blink response in rabbit eyes following central corneal epithelial debridement and administration of 0.01 mM (open circles), 0.1 mM (open diamonds) or 1.0 mM tetrodotoxin (open squares) (FIG. 3A) and of the fellow eyes treated with a vehicle only control (FIG. 3B);

FIG. 4 is a plot showing corneal blink response as a function of time in rabbit eyes with central corneal epithelial debridement treated with doses of 1.0 mM tetrodotoxin administered every 6 hours for 24 hours; and FIG. 5 is a plot showing the size of a corneal epithelial defect, in $mm^2$, as a function of time for untreated rabbit eyes (open squares) and for rabbit eyes treated with topical 1 mM tetrodotoxin every 8 hours (open diamonds).

FIG. 6 is a chart showing administration of TTX to produce corneal anesthesia of rabbit eyes post-excimer laser keratectomy as measured by a blink response test. Corneal sensation was tested at 3, 6, 9, 12, 15, 18, 21, 24, 30, 32 and 40 hours after excimer laser keratectomy. One 40 microliter drop of 1 mM TTX or vehicle (control) was administered at 0, 6, 12, 18 and 24 hours, as shown by the arrows. The results are graphed as the blink response (mean+/−SEM; N=6).

FIG. 7 is a chart showing the effect of topical administration of TTX on corneal wound healing following excimer laser keratectomy of rabbit eyes. Wound healing was assessed by measuring the size of the epithelial defect remaining at 24, 40, 49, 63, 68 and 72 hours after excimer laser keratectomy. The results are given as the area of the epithelial defect remaining in either the eyes treated with 1 mM TTX or the fellow eyes treated with the vehicle without TTX (control) (mean+/−SD; N=6).

FIG. 8 is a chart showing corneal anesthesia in abraded rabbit eyes following topical application of 20 microliters of 0.1 mM TTX. Corneal sensation was tested for TTX-treated and vehicle treated (control) eyes at 4 and 6 hours after a single topical administration of TTX or the control. The chart shows that a single 20 ul dose of 0.1 mM TTX, when applied to abraded rabbit corneas, resulted in 6 hours of local anesthesia as measured by the blink response.

FIG. 9 is a chart showing corneal anesthesia in abraded rabbit eyes following topical application of 20 microliters of 0.2 mM TTX. Corneal sensation was tested for TTX-treated and vehicle treated (control) eyes at 4, 6 and 8 hours after a single topical administration of TTX or the control. The chart shows that a single 20 ul dose of 0.2 mM TTX, when applied to abraded rabbit corneas, results in 8 hours of local anesthesia as measured by the blink response.

FIG. 10 is a chart showing corneal sensitivity after topical administration of a single dose of either 1 mM STX or vehicle (control) to abraded rabbit corneas as measured by blink response at 2, 4 and 6 hours after administration.

DETAILED DESCRIPTION OF THE INVENTION

I. Definitions

The following terms, as referred to herein, have the following meanings, unless otherwise indicated.

"Long-acting sodium channel blocking compound" refers to a compound, e.g. a toxin or analog that, when administered to a mammal in an effective concentration, causes local anesthesia lasting at least 3 to 10 hours, and specifically binds to the extracellular mouth of the sodium channel, occluding the channel by a mechanism separate from that of local anesthetics, such as lidocaine, proparacaine. See J. F. Butterworth and G. R. Strichartz, Anesthes. 72:711–734 (1990). Long-acting sodium channel blocking compounds, when administered in a single dose, may effect local anesthesia of long duration, lasting at least 3 hours (3 to 10 hours), preferably at least 4 hours (4–10 hours), and most preferably at least 6 to 10 hours. Such long-acting sodium channel blocking compounds include compounds that specifically bind to a site formed in part by an extracellular region of the alpha subunit of a sodium channel. See Goodman & Gilman's, The Pharmacological Basis of Therapeutics, Ninth Edition 340–341 (1996); H. Terlau, et al., Fed. Europ. Biochem. Soc. 293(1–2): 93–96 (1991); Encyclopedia of Molecular Biology, pages1127–1131 (ed. J. Kendrew 1994). Examples of long-acting sodium channel blocking compounds that bind to an extracellular site formed by the SS1 and SS2 segments of the alpha subunit include but are not limited to tetrodotoxin, saxitoxin, chiriquitoxin, GTTX (from G. tamarensis), gonyautoxins (GTX-I-V, GTX-I, GTX-II, GTX-III), neosaxitoxin, and derivatives and analogs thereof. D. J. Bower, et al., Clinical Toxicology, 18(7):813–863 (1981). Examples of long-acting sodium channel blocking compounds that bind to an extracellular site formed by the SS3 and SS4 segments of the alpha subunit, include but are not limited to alpha-scorpion toxin and sea anemone toxin. See Rogers, J. C. et al., J. Biol. Chem. 271(27):15950–15962 (1996).

"Saxitoxin" or "STX" refers to a compound comprising a tetrahydropurine moiety composed of two guanidine units fused together in a stable azaketal linkage, having a molecular formula $C_{10}H_{27}N_7O_4.2$—HCl, (mol. wt. 299.30) and to derivatives thereof, including but not limited to hydroxysaxitoxins and neosaxitoxin. Bower et al., Nonprotein Neurotoxins, Clin. Toxicol. 18(7):813–863 (1981).

"Tetrodotoxin" or "TTX" refers to the amino perhydroquinazoline compound having the molecular formula $C_{11}H_{17}N_3O_8$ and to derivatives thereof, including but not limited to anhydrotetrodotoxin, tetrodaminotoxin, methoxytetrodotoxin, ethoxytetrodotoxin, deoxytetrodotoxin and tetrodonic acid (Kao). Examples of TTX analogs include novel TTX analogs isolated from other organisms, as well as those that are partially or totally chemically synthesized. See e.g., Yotsu, M. et al. Agric. Biol. Chem., 53(3):893–895 (1989). Such analogs bind to the same site on the alpha subunit of sodium channels as does TTX.

"Anesthesia" refers to the loss of sensation, and, as used herein encompasses analgesia, the reduction in perceived pain without necessarily loss of sensation.

"Topical administration or topically administering" refers to application to a tissue of a mammal, including but not limited to application to epithelial tissue which has been damaged, lost or de-epithelialized.

"Epithelial tissue region" refers to an area of epithelial tissue in a mammal, where the epithelial layer is intact, damaged, or partially or completely absent.

"Pharmaceutically acceptable dose" refers to administration of an amount of a long-acting sodium channel blocking compound effective to achieve a local anesthetic effect for a clinically useful period of time.

"Opthalmically acceptable dose" refers to administration of an amount of a long-acting sodium channel blocking compound effective to achieve a local anesthetic effect in an eye for a clinically useful period of time.

II. Administration of Long-acting Sodium Channel Blocking Compounds

The invention is directed to a method of providing local anesthesia to a mammal experiencing pain in a tissue, preferably an epithelial tissue region. The method includes topically administering to the region, an effective dose of a long-acting sodium channel blocking compound in a suitable vehicle, including an opthalmically suitable vehicle.

In general embodiments of the invention, described in more detail below, the method provides local anesthesia to a patient having pain in an epithelial tissue region associated with damage or loss of epithelial tissue as a result of, for example, plastic surgery, canker sores, burns, sore throats, genital lesions, upper or lower gastrointestinal bronchoscopy or endoscopy, intubation, dermatologic abrasions or chemical skin peels.

In one preferred embodiment, the method is for producing local anesthesia in de-epithelialized corneal tissue in the eye of a patient after injury to the eye, for example, photorefractive keratectomy, by topically administering to the eye an effective dose of a long-acting sodium channel blocking compound in a suitable vehicle.

In experiments performed in support of the present invention, the use of tetrodotoxin as a topical anesthetic was demonstrated by administration to corneal epithelial tissue in rabbit eyes. Tetrodotoxin was administered to healthy rabbit eyes and to de-epithelialized rabbit eyes to determine the extent and duration of local anesthesia provided by tetrodotoxin and to evaluate its toxicity, as will be described below.

A. Administration in Healthy Rabbit Eyes

1. Administration of 0.1 mM, 1 mM and 10 mM tetrodotoxin

The extent and duration of local anesthesia provided by tetrodotoxin was determined by administration of the anesthetic at concentrations of 0.1 mM, 1 mM and 10 mM to healthy rabbit eyes. As described in Example 1, tetrodotoxin was administered to the right eye of 18 rabbits by instillation of 40 $\mu$l of the drug in a sodium citrate vehicle. The fellow, left eye of each rabbit received 40 $\mu$l of the sodium citrate vehicle as a control.

The anesthetic effect was determined by the corneal blink test, as described in Example 1. In this test, the cornea of each rabbit was mechanically stimulated and the rabbit's response was scored on a scale of 1–3, where a score of 1 was assigned for no blink, a score of 2 was assigned for a partial blink without full lid closure and a score of 3 was assigned for a full blink. Each eye was scored prior to administration of the drug and at intervals after administration for 8 hours.

FIG. 1A shows the results of administration of tetrodotoxin, where the response score is plotted as a function of time after administration of 0.1 mM (open circles), 1 mM (open diamonds) and 10 mM (open squares) tetrodotoxin. At a concentration of 0.1 mM tetrodotoxin, no local anesthesia was produced in the rabbits, as evidenced by the response scores of 2.8–3.0.

The 1 mM tetrodotoxin formulation produced local anesthesia in all of the animals, as evidenced by the one minute score of 1.17. The local anesthesia effect was relatively short-lived, as evidenced by the 1 hour score of 1.5 and by the 3 hour score of 2.83.

The 10 mM tetrodotoxin formulation produced longer-lasting local anesthesia. At one minute after administration, all rabbit corneas werelocally anesthetic with a mean anesthesia score of 1.0 (SD=0). At 4 hours, local anesthesia was still present with a mean score of 1.17 (SD=0.4 1), and by 8 hours, the mean score of 2.0 indicated residual local anesthesia in most animals. As late as 8 hours, 5 of 6 rabbits showed some residual local anesthesia.

Figure 1B:
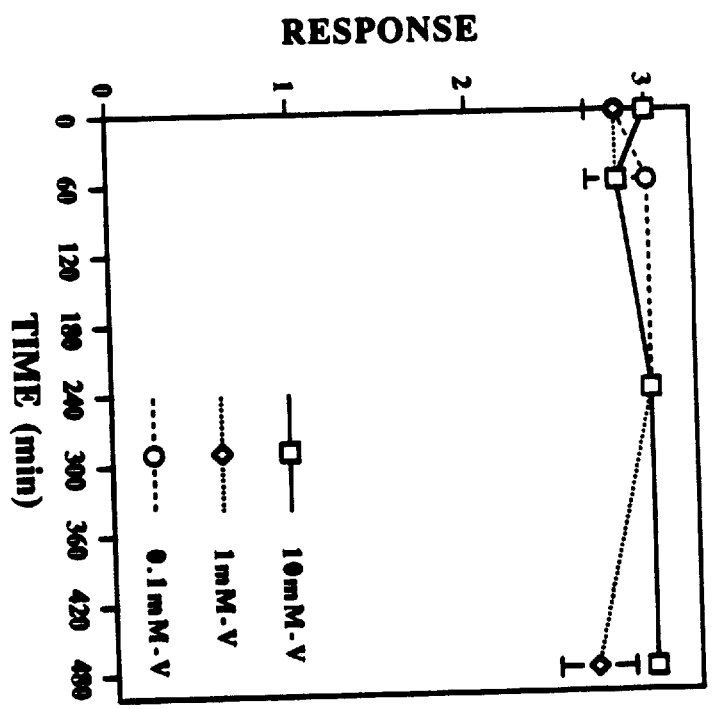

FIG. 1B shows the corneal response scores following administration of the placebo control vehicle. As seen, corneal blink response remained at a score of about 3, indicating that none of the eyes treated with the control vehicle had diminished corneal sensitivity.

2. Comparative Test

In a separate experiment (Example 1B), the anesthetic duration provided by tetrodotoxin (10 mM and 1 mM) was compared to that provided by 0.5% proparacaine, a common topical ocular anesthetic (Rosenwasser). Following the procedure set forth in Example 1, the right eye of each of the 18 test rabbits received 40 μl of the test drug with the fellow, left eye of each rabbit receiving a placebo control. The results are shown in FIGS. 2A and 2B.

Figure 2A:
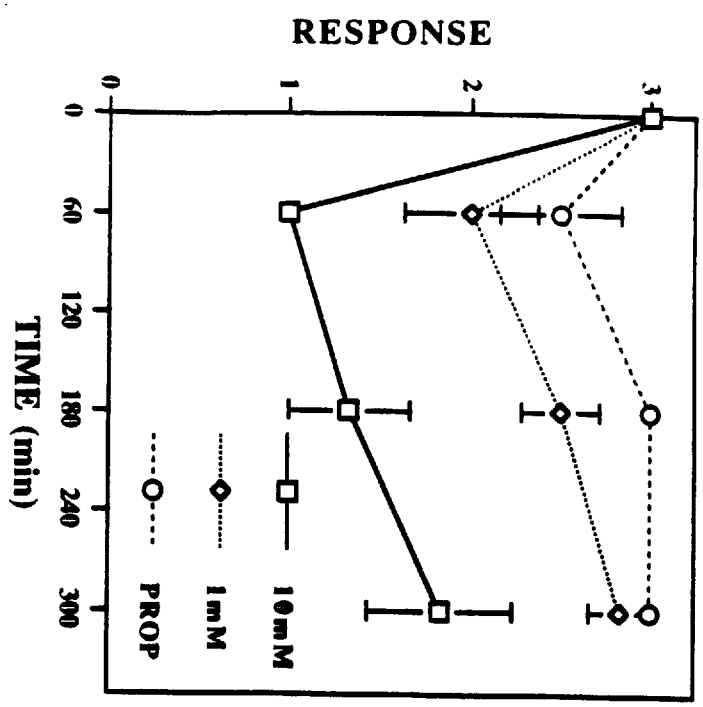
Figure 2B:
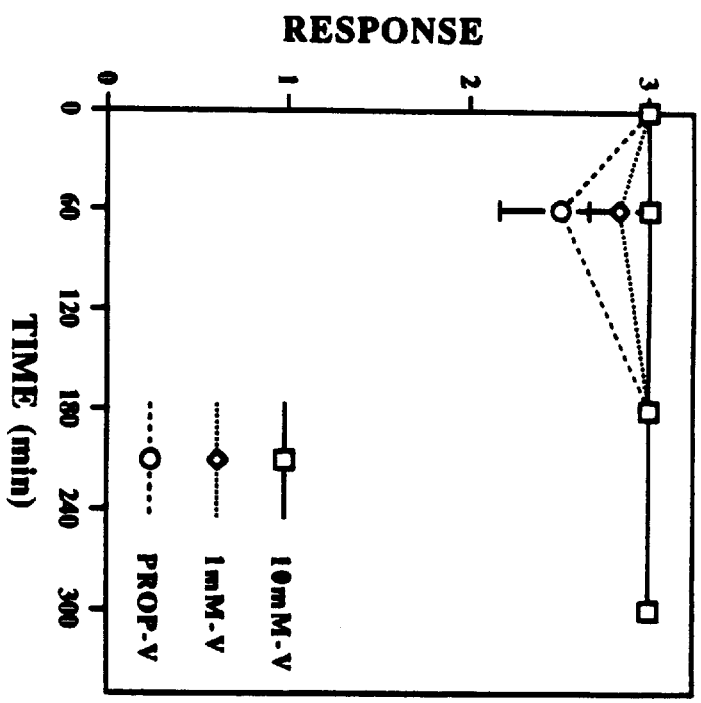

As seen in FIG. 2A, the 10 mM tetrodotoxin dose (open squares) produced significantly longer local anesthesia than proparacaine (open circles). While proparacaine produced local anesthesia in 6 of 6 rabbits at 1 minute (Table 2), by 1 hour the mean blink response score had increased to 2.50 (SD+0.84), and at 3 hours, all eyes receiving proparacaine had normal sensation. In contrast, as late as 5 hours, 4 of 6 rabbits receiving tetrodotoxin showed some residual local anesthesia with a mean score of 1.83, which was significantly different (p=0.0325, Wilcoxon test) from the mean score of 3.00 obtained with proparacaine at 5 hours.

3. Slit Lamp Examination, Pachometry, Toxicity

To assess whether administration of tetrodotoxin causes clinical alterations in the cornea, the eyes of animals treated with 10 mM and 1 mM tetrodotoxin were examined at 12 and 24 hours after drug administration by slit lamp biomicroscopy with a portable Kowa slit lamp, with and without fluorescein stain from impregnated strips moistened with balance salt solution. There was no apparent ocular irritation or epithelial toxicity after administration, nor was there any obvious discomfort, as evidenced by prolonged eye closure or repetitive blinking.

To evaluate whether endothelial function was significantly affected by administration of tetrodotoxin, pachometry (Humphrey Pachometer) readings prior to and 24 hours after tetrodotoxin administration were performed on animals treated with 10 mM and 1 mM tetrodotoxin. Pachometry readings on rabbit eyes receiving the highest doses of tetrodotoxin showed no evidence of corneal thickening during the 24 hour observation period, as shown in Table 3 in Example 1B.

With respect to systemic toxicity, each test rabbit was observed carefully for any signs of systemic toxicity during the 24 hour test period. No rabbit had any alterations of feeding, movement, respiration, or alertness during this period that might suggest a toxic effect of tetrodotoxin. No rabbit died or was noted to have abnormalities in behavior.

Collectively, and in summary, these experiments demonstrate that tetrodotoxin, administered topically by instillation of drops into the eye, provides an anesthetic effect. The dosage administered from the 10 mM tetrodotoxin formulation achieved corneal anesthesia with a rapid onset and anesthetic duration for nearly 4 hours, with some anesthetic effect, as evidenced by reduced corneal sensation, provided for at least 8 hours, a significant improvement over that provided by proparacaine. The tests also showed a dose response effect, with lower doses producing either shorter or no anesthetic effect. Importantly, there was no apparent signs of ocular irritation, corneal thickening or systemic toxicity after administration of tetrodotoxin.

B. Administration in De-epithelialized Rabbit Eyes

In other experiments performed in support of the invention, tetrodotoxin was administered to de-epithelialized rabbit corneas. As set forth in Example 2A, a central epithelial corneal abrasion was created in each eye and tetrodotoxin, at a concentration of 0.1 mM, 1 mM or 10 mM, was administered into the inferior conjunctival cul-de-sac of one eye. A control vehicle was administered into the fellow eye.

Corneal sensation was tested, as described in Example 2A, and the rabbit's response was scored as described above on a scale of 1–3, with a score of 3 indicating full responsiveness and a score of 1 indicating full local anesthesia. Corneal sensation was tested prior to administration of tetrodotoxin and after administration at 2, 4, 6 and 8 hours (Example 2B).

Figure 3A:
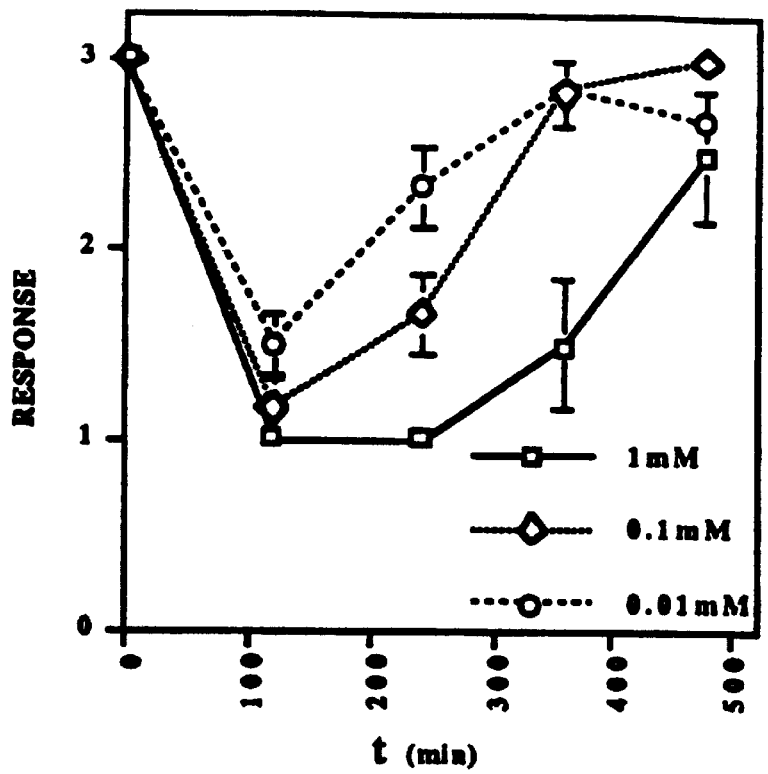
Figure 3B:
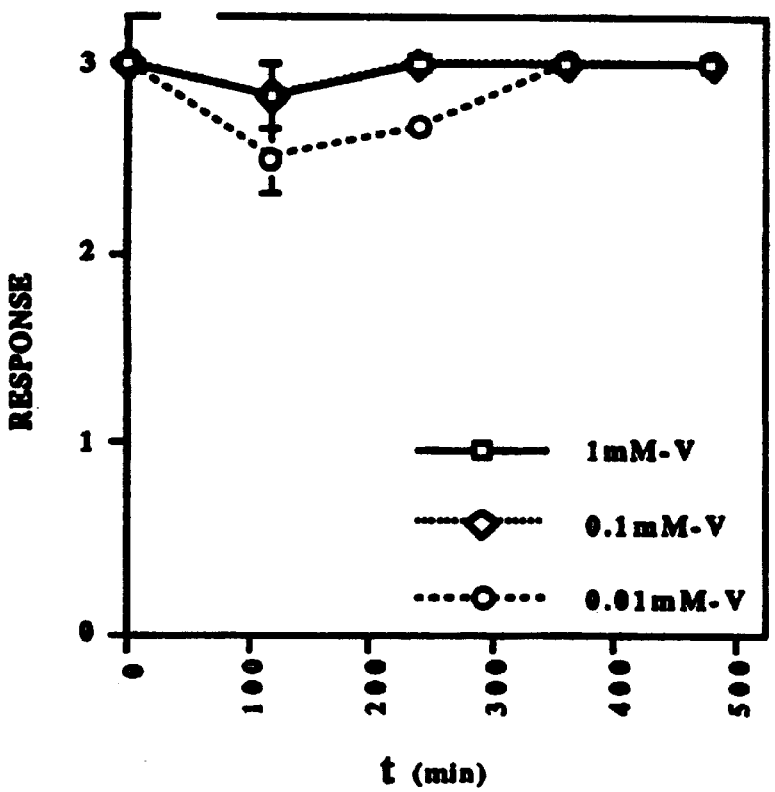

FIG. 3A shows corneal blink response in centrally de-epithelialized rabbit corneas treated with topical 0.01 mM (open circles), 0.1 mM (open diamonds) or 1.0 mM tetrodotoxin (open squares). FIG. 3B shows the corneal blink response for the fellow, left eyes treated with the vehicle only control.

As seen in FIG. 3A, tetrodotoxin induced local anesthesia of de-epithelialized corneas varied as a function of dose. At 2 hours after tetrodotoxin application, all of the tetrodotoxin concentrations showed some anesthetic effect. At 4 hours, rabbit eyes that were treated with 1.0 mM and 0.1 mM tetrodotoxin were significantly different, with mean anesthesia scores of 1.00 (SDD=0.00, P=0.0011) and 1.67 (SD= 0.52, P=0.0011), respectively. At 6 hours after tetrodotoxin administration, 5 of 6 rabbit eyes treated with 1.0 mM tetrodotoxin were anesthetic with a mean response score of 1.50 (SD=0.84, P=0.0076). By 8 hours the mean response score for 1.0 mM tetrodotoxin was 2.50 (SD=0.84), with 2 of 6 rabbits showing significantly reduced sensation.

The rabbits were observed for changes in feeding habits, movement, respiration and alertness for 24 hours, with no apparent changes observed.

The effectiveness of tetrodotoxin produced by repeated dosing was determined, as described in Example 2C. Tetrodotoxin at a concentration of 1 mM was administered every 6 hours to the centrally de-epithelialized cornea of six rabbits for 24 hours. Corneal sensation was measured every 3 hours for 30 hours.

Figure 4:
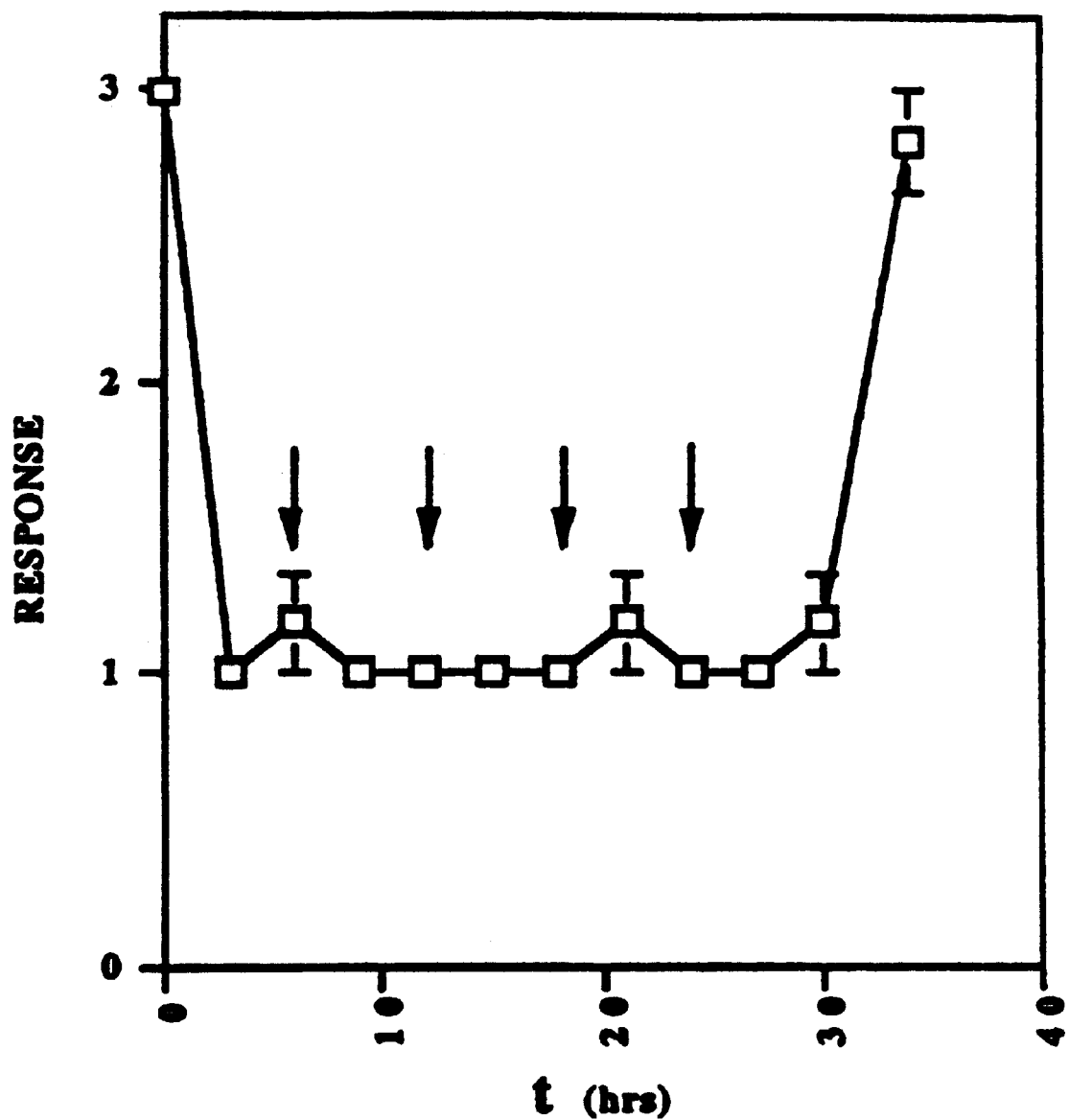

The results, plotted in FIG. 4, show that at 3 hours after the first dose of tetrodotoxin (at t=0) all of the rabbit eyes were anesthetic with a mean response score of 1.00 (SD= 0.00, P=0.0011). All six rabbit eyes remained anesthetic for the duration of the experiment, with the 40 μl dose of 1 mM tetrodotoxin administered every six hours as indicated by the arrows in the figure. The mean response scores range from 1.00 to 1.17 (P=0.0011) over the 24 hour period of administration. At 6 hours after the final dose of tetrodotoxin (30 hours after the initial dose), 6 of 6 rabbit eyes were still anesthetic with a mean response score of 1.17 (SD=0.41, P=0.0011). At 10 hours after the final dose (34 hours after the initial dose), 5 of 6 rabbit eyes had normal sensation with a mean response score of 2.83 (SD=0.41).

The results presented in FIGS. 3 and 4 show that tetrodotoxin is an effective anesthetic at a dosage provided by the 1 mM formulation in partially de-epithelialized corneas. The dose required for effective local anesthesia is significantly reduced in de-epithelialized tissues compared to intact corneas, as evidenced by comparing FIG. 1A with FIG. 3. The effective dose administered from the 1 mM formulation in rabbits is approximately 1% of the lethal human dose, as discussed in more detail below.

The studies also show that tetrodotoxin administered every 6 hours for 24 hours from formulation having a 1 mM concentration of tetrodotoxin produced local anesthesia for greater than 30 hours and that, at this dosing frequency, a reduction in corneal sensation was observed for 30 hours.

C. Re-epithelialization of Tissue

As discussed above, ocular pain after a photorefractive keratectomy procedure is severe for 24–48 hours and characterized by throbbing, watering and foreign body sensations. Conventional treatment includes topical application of non-steroidal anti-inflammatory drugs, low dose topical anesthetics, oral analgesics or bandage soft contact lens. See R. Lim-Bon-Siong, et al., Efficacy and Safety of the ProTek (Vifilcon A) Therapeutic Soft Contact Lens After Photorefractive Keratectomy, Am. J. Opthalmology, 125:169–176 (1998). It has been shown that frequently applied topical anesthetics inhibit corneal re-epithelialization (Rosenwasser).

To determine the effect of tetrodotoxin on corneal re-epithelialization, 1 mM tetrodotoxin was administered to rabbit corneas having an epithelial defect. The epithelial defect was created in the right eye of 12 rabbits using n-heptanol soaked filter paper discs, as described in Example 3. The rabbits were randomized into two test groups for treatment with 40 $\mu$l of 1 mM tetrodotoxin every 8 hours or for no treatment. The size of the defect was measured in both test groups at regular intervals after creation of the defect. The results are shown in FIG. 5.

As seen in FIG. 5, corneal defects of corneas left untreated and of corneas treated with tetrodotoxin were essentially identical in their rates of healing. By 49 hours, 4 of 6 untreated and 3 of 6 tetrodotoxin-treated corneas were completely healed. At 56 hours, 4 of 6 untreated and 4 of 6 tetrodotoxin-treated corneas were completely healed. By 66 hours, all but one cornea from each group had completely healed.

To determine if tetrodotoxin treatment had altered corneal thickness, pachometry was performed 90 hours after the initial wound was created. There was no statistical difference in corneal thickening between untreated and tetrodotoxin-treated corneas.

This experiment shows that topical tetrodotoxin administered every 8 hours had no effect on corneal re-epithelialization compared to untreated control rabbit eyes. The rate of healing was nearly identical for the two groups, and tetrodotoxin had no apparent effect on corneal thickness compared to untreated control eyes.

III. Method of Administration

As discussed above, the present invention provides a method of producing local anesthesia in a subject experiencing pain in an epithelial tissue region, typically an epithelial tissue region that is damaged or is partially or completely absent, by administering a therapeutically effective dose of tetrodotoxin.

Tetrodotoxin is a nonprotein neurotoxin which is found in multiple diverse animal species, including puffer fish, porcupine fish, goby fish, newts, frogs and the blue-ringed octopus (Bower). Tetrodotoxin and its anesthetic properties have been reviewed (Blakenship, Kao, Ogura).

In the experiments described above, tetrodotoxin was administered topically to the cornea of rabbit eyes and found to provide long-acting pain relief with no signs of systemic or local toxicity.

More generally, the method of the present invention is intended for use in providing local anesthesia for pain associated with any epithelial tissue region in a subject, for example, pain associated with epithelial ulcers, such as a canker sore or genital lesions. Canker sores can occur alone or in groups on the inside of the cheek or lip or underneath the tongue. Severely affected people have continuously recurring ulcers which last for one to two weeks (Clayman). Long-acting, topical painkillers, such as tetrodotoxin, can ease the pain without significantly retarding healing of these oral lesions.

Genital ulcers are usually caused by sexually transmitted diseases, including herpes and syphilis. The early stages of syphilis are characterized by a hard chancre, a painful ulcer where bacteria has penetrated the skin. This may be followed by shallow, elongated ulcers once the chancre has healed. Such ulcers are painful. Genital ulceration may also be a side effect of drugs taken orally or caused by solutions applied to genital warts. Tetrodotoxin administered in accordance with the method of the invention provides relief from the pain associated with such ulcers.

Pain in epithelial tissue is also caused by burns. Burns affecting the epidermal layer are usually associated with pain, restlessness and fever. Treatment of such a burn in accordance with the method of the invention can provide relief from the attendant pain, while allowing epithelial healing.

Pain as a result of damage to or loss of epithelial tissue is also associated with other conditions and procedures, such as sore throats and plastic surgery, for example carbon dioxide laser surgery to remove for skin resurfacing and removal of wrinkles (Rosenberg), burns, genital lesions, upper or lower gastrointestinal bronchoscopy or endoscopy, intubation, dermatologic abrasions or chemical skin peels. Tetrodotoxin administered in accordance with the method of the invention is beneficial in relieving pain associated with such damaged tissues without significantly retarding healing.

A. Tetrodotoxin and Saxitoxin Formulations and Dosages

For use in the eye, tetrodotoxin and saxitoxin are typically administered in an aqueous solution, which may be an aqueous suspension, an ointment, a gel or an aqueous polymer solution. Preferably, the solution has a pH of between 4–8, more preferably between about 5–7.5. Such ophthalmic formulations suitable for topical and intraocular administration can be formulated in accordance with techniques known to those of skill in the art.

Typically, the active ingredient tetrodotoxin or saxitoxin is formulated into purified water or a physiological saline solution as a major vehicle. However, it will be appreciated that the ophthalmic formulation can contain other components, including, but not restricted to, buffering means to maintain or adjust pH, such as acetate buffers, citrate buffers, phosphate buffers and borate buffers; viscosity increasing agents such as polyvinyl alcohol, celluloses, such as hydroxypropyl methyl cellulose and carbomer; preservatives, such as benzalkonium chloride, chlorobutanol, phenylmercuric acetate and phenyl mercuric nitrate; tonicity adjustors, such as sodium chloride, mannitol and glycerine; and penetration enhancers, such as glycols, oleic acid, alkyl amines and the like. The addition of a vasoconstrictor to the formulation is also contemplated. Combination formulations comprising said long-acting sodium channel blocking compound and an antibiotic, a steroidal or a non-steroidal anti-inflammatory drug are also contemplated.

The ophthalmic formulation may also be a suspension of particles, such as polymer particles or liposomes, for entrapping the active compound. For example, polymer particles prepared by suspension or emulsion polymerization to have a particle size of below about 50 $\mu$m, for entrapping the active compound or for increasing viscosity can be added to the formulation.

The final ophthalmic formulations in unit dosage form are preferably stored in opaque or brown containers to protect then from light exposure. Multi-dose containers can also be used, if desired, particularly if the final formulation has a low viscosity to permit constant, accurate dosages to be administered dropwise to the eye.

The method of the invention, more generally, provides local anesthesia to mucous membranes or damaged, e.g., abraded, skin by topical administration of tetrodotoxin or saxitoxin in the form of solutions, creams, ointments, gels, aerosols or the like. Such formulations are prepared using ingredients and according to procedures known to those of skill in the art or as described in, for example, REMINGTON'S PHARMACEUTICAL SCIENCES.

Administration of tetrodotoxin has been well studied in a number of animal species (Kao), and the lethal oral dose in humans has been estimated to be about 10–18 μg/kg (Kao). For a 70 kg person, the lethal dose would therefore be 0.7–1.26 mg.

In the experiments performed in support of the present invention, described above, a 40 μl aliquot of 0.01 mM, 1 mM or 10 mM tetrodotoxin was administered topically to rabbits' eyes. This corresponds to a dosage of between 0.127–127 μg of tetrodotoxin, well below the lethal oral human dose and giving a sufficient safety margin to allow for any differences in systemic absorption between topical and oral administration. In additional experiments, 20 μl aliquots of 0.1 mM and 0.2 mM tetrodotoxin were administered topically to partially de-epithelialized rabbit eyes, resulting in 6 and 8 hours of local anesthesia respectively.

For administration to the eye, the tetrodotoxin formulation, as a concentration of between 0.001–10 mM and in the form of aqueous solution, suspension, ointment or the like, is administered dropwise to the eye. A single drop typically administers between 10–50 μl. The drop volume and solution concentration, of course, determine the dosage delivered, which, for the ranges specified here, is between about 0.003–160 μg.

Saxitoxin (1 mM) was administered in a 20 μl dose to partially de-epithelialized rabbit corneas, resulting in 4 hours of local anesthesia. This dosage of saxitoxin corresponds to approximately 5.9 μg of saxitoxin, well below the estimated human lethal dose (oral) of between 300 μg to 1.0 mg. See Bower et al., Clin. Toxicol., 18(7):813–863 (1981).

For administration to the eye, the saxitoxin formulation, as a concentration of between 0.001–10 mM and in the form of aqueous solution, suspension, ointment or the like, is administered dropwise to the eye. A single drop typically administers between 10–50 μl. The drop volume and solution concentration, of course, determine the dosage delivered, which, for the ranges specified here, is between about 0.003 to 149 μg.

It will be appreciated that the dose and concentration of tetrodotoxin or saxitoxin administered is determined on an individual basis, with consideration given to such factors as age and body weight of the patient, as well as to the route of administration and the clinical anaesthetic requirements.

Preferably, tetrodotoxin or saxitoxin is administered topically to the painful epithelial tissue region by application of a formulation having a tetrodotoxin or saxitoxin concentration of between about 0.001–10 mM. The actual dosage of tetrodotoxin or saxitoxin administered will, of course, depend on the amount of formulation applied and the surface area over which it is applied.

The dosing regimen is selected to provide pain relief as needed for a particular clinical condition. Often, pain is most intense in the first 24–72 hours following damage to the tissue, by a surgical procedure or other trauma, and administration every 6 hours during this time period is effective to provide a long-acting anesthetic effect. This was demonstrated in the experiment discussed above where tetrodotoxin was administered every 6 hours for 24 hours to achieve greater than 30 hours of local anesthesia in rabbits, with no signs of irritation or toxicity.

It will be appreciated that topical administration of either tetrodotoxin or saxitoxin may be combined with conventional modes of pain relief, such as administration of oral or topical non-steroidal anti-inflammatory drugs or antibiotics and the use of bandage soft contact lens in ocular applications. For example, methods of the invention include applying to the corneal surface of an eye of a mammal, a bandage contact lens, wherein said lens is capable of delivering an opthalmically effective dose of said long-acting sodium channel blocking compound to said corneal surface. One of skill in the art will appreciate that the there are a number of ocular drug delivery systems and methods that can be used with the present invention, some of which are described in Lee, V. and Robinson, J. R., Review: Topical Ocular Drug Delivery: Recent Developments and Future Challenges, J. Ocular Pharmacol. 2(1):67–108 (1986) (incorporated herein by reference).

Moreover, another preferred method of producing anesthesia in an eye of a mammal comprises topically administering to the corneal surface of an eye of a mammal an opthalmically effective dose of proparacaine or other comparable local anesthetic, including tetracaine or benoxinate, in an opthalmically acceptable vehicle before administering to said eye, an opthalmically effective dose of a long-acting sodium channel blocking compound in an opthalmically acceptable vehicle. Prior administration of proparacaine or other comparable local anesthetic, to the eye of a mammal effectively diminishes the production of tears by the eye, preparing the eye for topical administration of a long-acting sodium channel blocking compound, such as TTX or STX. By decreasing tearing and anesthetizing the corneal surface of an eye, the prior administration of proparacaine, tetracaine or benoxinate, decreases the amount of the long-acting sodium channel blocking compound that would wash away with tears. Thus, the method enables administration of lower effective doses of the long-acting sodium channel blocking compound. For example, dosages of proparacaine range from 0.05% to 0.5%, and preferably, from 0.05 to 0.1% formulations in any opthalmically acceptable vehicle.

From the foregoing, it can be appreciated how various features and objects of the invention are met. The method of the invention provides an effective, long-lasting local anesthesia by topical administration of a long-acting sodium channel blocking compound to a painful epithelial tissue region. The studies reported herein illustrate, using a rabbit model, that a single dose of tetrodotoxin at a concentration of 1 mM or 10 mM achieves local anesthesia with rapid onset and for at least 8 hours. A repeated dosing regimen is effective to produce local anesthesia for greater than 30 hours. Importantly, no evidence of either ocular or systemic toxicity in the test animals was observed at any of the dosage levels, including 10 mM tetrodotoxin. Moreover, a single dose of saxitoxin at a concentration of 1 mM achieves local anesthesia upon administration to a partially abraded cornea with rapid onset and for at least 4 hours.

One of skill in the art will appreciate that any of the long-acting sodium channel blocking compounds can be used according to the methods and procedures described herein to determine pharmaceutically or opthalmically effective doses and other aspects of the invention.

VI. EXAMPLES

The following examples illustrate the methods and compositions of the invention, but are in no way intended to limit the invention.

Materials: Tetrodotoxin was purchased from Sigma Chemical Co. (St. Louis, Mo.) in vials containing 1 mg tetrodotoxin and approximately 5 mg sodium citrate buffer, pH=4.3, in lyophilized form.

Saxitoxin and additional tetrodotoxin was purchased from Alexis Chemicals.

Example 1

Administration of Tetrodotoxin to Healthy Rabbit Eyes

A. 0.1 mM, 1 mM and 10 mM Tetrodotoxin

Tetrodotoxin formulations of 0.1 mM, 1 mM and 10 mM were prepared in a 60 mM sodium citrate carrier at pH 4.3.

Eighteen New Zealand white rabbits were divided into three groups of six rabbits. Each rabbit received a 40 μl aliquot of one of the tetrodotoxin formulations into the inferior conjunctival cul-de-sac of the right eye, with the left fellow eye receiving 40 μl of the pH 4.3 60 mM sodium citrate carrier as a control.

Corneal sensation was tested with a 4-0 silk suture mounted upon a wooden cotton tip applicator such that the suture extended 5 mm beyond the wooden end of the applicator. The cornea was mechanically stimulated centrally three times with the suture to produce grossly visible indentation of the cornea as the endpoint (similar to previous rabbit model of corneal anesthesia reported in Maurice D M, Singh T., The absence of corneal toxicity with low-level topical anesthesia. Am J Ophthamol. 99:691–696. (1985)). Care was taken not to stimulate the eyelashes. The rabbit's response was graded in the following fashion: no blink=1; partial blink without full eyelid closure=2; fuill blink=3. Thus, a score of 3 indicates full responsiveness and a score of 1 indicates full local anesthesia. The highest anesthesia score of the 3 tests was recorded for each time point.

Corneal sensation was tested prior to administration of drugs and again at 1 minute, 1 hour, 4 hours and 8 hours. The results are tabulated in Table 1 below and shown in FIGS. 1A–1B. Statistical analysis was by the non-parametric Wilcoxon test with a statistical sugnificance of p-<0.05.

B. Comparative Study: 1 mM, 10 mM Tetrodotoxin and Proparacaine

Eighteen New Zealand white rabbits were divided into three groups of six rabbits. Each rabbit received a 40 μl aliquot into the inferior conjunctival cul-de-sac of the right eye of 1 mM or 10 mM tetrodotoxin or of proparacaine 0.5% (Ophthetic). The left fellow eye received 40 μl of a placebo, control vehicle (60 mM, pH 4.3 sodium citrate).

Following the procedure described in Example 1A, the anesthetic duration was determined by measuring corneal blink response in the test rabbits at 0 min, 1 minute, 1 hour, 3 hours and 5 hours. The results are tabulated in Table 2 and shown in FIGS. 2A–2B.

TABLE 2

| | Mean Blink Response (N = 6) | | | | |
|---|---|---|---|---|---|
| Drug Treatment | 0 min. | 1 min. | 60 min. | 180 min. | 300 min. |
| Proparacaine | 3.00 (0.00) | 1.00 (0.00) | 2.50 (0.84) | 3.00 (0.00) | 3.00 (0.00) |
| Proparacaine/control | 3.00 (0.00) | 3.00 (0.00) | 2.50 (0.84) | 3.00 (0.00) | 3.00 (0.00) |
| 1 mM tetrodotoxin | 3.00 (0.00) | 2.17 (0.75) | 2.00 (0.89) | 2.50 (0.55) | 2.83 (0:41) |
| 1 mM tetrodotoxin/control | 3.00 (0.00) | 3.00 (0.00) | 2.83 (0.41) | 3.00 (0.00) | 3.00 (0.00) |
| 10 mM tetrodotoxin | 3.00 (0.00) | 1.00 (0.00) | 1.00 (0.00) | 1.33 (0.82) | 1.83 (0.98) |
| 10 mM tetrodotoxin/control | 3.00 (0.00) | 3.00 (0.00) | 3.00 (0.00) | 3.00 (0.00) | 3.00 (0.00) |

*numbers in parenthesis are standard deviation of mean blink response for n = 6.

The extent and duration of local anesthesia after topical TTX was administered to intact rabbit corneas varied as a function of dose (FIG. 1A, Table 1). At 0.1 mM TTX, only partial local anesthesia was produced in 2 of 6 rabbits. At 1 mM TTX, local anesthesia initially was produced in 6 of 6 animals but the effect was generally short-lived. At one minute after administration of TTX, the mean anesthesia score was 1.17 (SD=0.41). At 1 hour the score was 1.50 (SD=0.84) and by 3 hours the mean score had increased to 2.83 (SD=0.41). At 6 hours the TTX-vehicle had a better anesthetic score than the 1 mM TTX treated eyes. However, neither of these scores were significantly different from each other or from the pretreated eyes anesthesia score of 3.0. (SD=0).

At 10 mM, TTX produced a more reproducible and longer lasting local anesthesia. At one minute after administration, all rabbit corneas were anesthetic with a mean anesthesia score of 1.00 (SD=0). At 4 hours, local anesthesia was still present with a mean score of 1.17 (SD=0.41). As late as 8 hours, 4 of 6 rabbits showed some residual local anesthesia

TABLE 1

| | Mean Blink Response (N = 6) | | | | |
|---|---|---|---|---|---|
| Drug Treatment | 0 min. | 1 min. | 60 min. | 240 min. | 480 min. |
| 0.1 mM tetrodotoxin | 2.83 (0.41) | 2.67 (0.52) | 2.67 (0.82) | 3.00 (0.00) | 2.83 (0.41) |
| 0.1 mM tetrodotoxin/control | 2.83 (0.41) | 3.00 (0.00) | 3.00 (0.00) | 3.00 (0.00) | 3.00 (0.00) |
| 1 mM tetrodotoxin | 2.83 (0.41) | 1.17 (0.41) | 1.50 (0.84) | 2.83 (0.41) | 2.83 (0.41) |
| 1 mM tetrodotoxin/control | 2.83 (0.41) | 2.83 (0.41) | 2.83 (0.41) | 3.00 (0.00) | 2.67 (0.52) |
| 10 mM tetrodotoxin | 3.00 (0.00) | 1.00 (0.00) | 1.00 (0.00) | 1.17 (0.41) | 2.00 (0.89) |
| 10 mM tetrodotoxin/control | 3.00 (0.00) | 3.00 (0.00) | 2.83 (0.41) | 3.00 (0.00) | 3.00 (0.00) |

*numbers in parenthesis are standard deviation of mean blink response for n = 6.

with a mean score of 2.00 (SD=0.89). This was significantly different, (P=0.0325), from the mean score of 3.00 (SD=0) obtained with vehicle alone at 8 hours (Table 1).

The anesthetic duration of 10 mM TTX was compared to that of 1 mM TTX, and proparacaine (FIG. 2, Table 2). At the 10 mM dose, TTX produced significantly longer local anesthesia than proparacaine. While proparacaine produced local anesthesia in 6 of 6 rabbits at 1 minute, by 1 hour the mean score had increased to 2.50 (SD=0.84), and at 3 hours, all eyes receiving proparacaine had normal sensation. As late as 5 hours, 4 of 6 rabbits receiving TTX showed some residual local anesthesia with a mean score of 1.83 (SD=0.98). This was significantly different, (P=0.0325), from the mean score of 3.00 (SD=0) obtained with proparacaine or vehicle alone at 5 hours (Table 2).

C. Pachometry

To evaluate whether endothelial function was significantly affected by administration of 10 mM or 1 mM TTX, pachometry readings were made (Humphrey Pachometer, Humphrey Instr., San Leandro, Calif.) prior to and 24 hours after TTX administration. The results are given in Table 3 as mean corneal thickness, with the standard deviation indicated in parenthesis. Pachometry readings on rabbits receiving the highest doses of TTX showed no evidence of corneal thickening during the 24 hour observation period.

TABLE 3

| Drug | Corneal Thickness (mm) | |
|---|---|---|
| Treatment | 0 hrs. | 24 hrs. |
| proparacaine | 0.38 (0.03) | 0.38 (0.04) |
| proparacame/control | 0.39 (0.04) | 0.38 (0.03) |
| 1 mM tetrodotoxin | 0.39 (0.04) | 0.39 (0.04) |
| 1 mM tetrodotoxin/control | 0.36 (0.01) | 0.39 (0.04) |
| 10 mM tetrodotoxin | 0.38 (0.03) | 0.37 (0.01) |
| 1 mM tetrodotoxin/control | 0.36 (0.01) | 0.38 (0.04) |

*numbers in parenthesis are standard deviation of mean corneal thickness for n = 6.

Drug treatments labelled "/control" represent fellow eyes of either proparacaine or TTX-treated eyes, wherein the fellow eyes were treated with the citrate vehicle alone.

Slit Lamp Examination and Fluorescein Staining.

Slit lamp biomicroscopy with a portable slit lamp (Kowa SL-5, Kowa Company, Japan) was performed with and without fluorescein stain from impregnated strips moistened with balance salt solution at 12 and 24 hours after topical administration.

To assess whether TTX administration caused clinical alterations in the cornea, all animals were examined with a slit lamp after fluorescein staining. Despite the acidic vehicle, TTX administration did not cause any apparent ocular irritation after administration. There was no obvious discomfort in any of the rabbits evidenced by prolonged eye closure or repetitive blinking. No ocular injection was noted during the 24 hour observation period. At 3 hours most of the rabbits had a mild central punctuate epithelial keratopathy in the area of corneal sensation testing, but there was no difference between rabbits receiving proparacaine and TTX. By 24 hours, all signs of epithelial damage had disappeared by slit lamp examination and fluorescein staining.

Toxicity

The rabbits were observed for changes in feeding habits, movement, respiration and alertness during the first 24 hours by the experimenters and for the subsequent week daily by animal care personnel.

No rabbit had any alterations of feeding, movement, respiration, or alertness during this period that suggested a toxic effect of the TTX. No rabbit died or was noted to have abnormalities in behavior by the animal care personnel for 7 days subsequent to TTX administration.

Example 2

Topical Administration of Tetrodotoxin to Partially De-epithelialized Rabbit Corneas A. Corneal Abradement and Blink Response Test After general anesthesia and topical application of 0.5% proparacaine to each eye, a #69 Beaver blade was used to create a central epithelial defect which measured between 3.0–3.5 mm diameter in both eyes of each test rabbit.

Corneal sensation was tested with a 4-0 silk suture mounted upon a wooden cotton tip applicator such that the suture extended 5 mm beyond the wooden end of the applicator. Because the central cornea was often rendered largely anesthetic following mechanical epithelial debridement, the cornea was stimulated in the mid-peripheral cornea, outside of the abraded area, with the suture to produce grossly visible indentation of the cornea as the endpoint. Care was taken not to stimulate the eyelashes. The rabbit's response was graded in the following fashion; no blink=1, partial blink without full eyelid closure=2, full blink=3.

B. Dose Response

Tetrodotoxin in a pH 4.3 sodium citrate vehicle was formulated into concentrations of 1 mM, 0.1 mM, and 0.01 mM.

New Zealand white rabbits were divided into three experimental groups of six. Each rabbit received a 40 µl aliquot of tetrodotoxin at a concentration of 0.01 mM, 0.1 mM or 1 mM into the inferior conjunctival cul-de-sac of the right eye. A 40 µl of a pH 4.3 sodium citrate vehicle as a control into the fellow, left eye.

Corneal sensation was tested prior to administration of tetrodotoxin and after administration at 2, 4, 6 and 8 hours. The results, presented as the mean score for the 6 rabbits in each test group, are tabulated below in Table 4 and shown in FIGS. 3A–3B, where FIG. 3A shows the response scores for eyes treated with tetrodotoxin and FIG. 3B shows the response scores for the fellow, control-vehicle treated eyes. Statistical analysis using the Wilcoxon test was performed by comparing the tetrodotoxin treated eyes to the pre-operative anesthesia response score.

TABLE 4

| Drug | Mean Blink Response (N = 6) | | | |
|---|---|---|---|---|
| Treatment | 2 hrs. | 4 hrs. | 6 hrs. | 8 hrs |
| 1.0 mM tetrodotoxin | 1.00 (0.00) | 1.00 (0.00) | 1.50 (0.84) | 2.50 (0.84) |
| 1.0 mM tetrodotoxin/ control | 2.83 (0.41) | 3.00 (0.00) | 3.00 (0.00) | 3.00 (0.00) |
| 0.1 mM tetrodotoxin | 1.17 (0.41) | 1.67 (0.52) | 2.83 (0.41) | 3.00 (0.00) |
| 0.1 mM tetrodotoxin/ control | 2.83 (0.41) | 3.00 (0.00) | 3.00 (0.00) | 3.00 (0.00) |
| 0.01 mM tetrodotoxin | 1.50 (0.84) | 2.33 (0.82) | 2.83 (0.41) | 2.67 (0.52) |
| 0.01 mM tetrodotoxin/ control | 2.50 (0.84) | 2.67 (0.52) | 3.00 (0.00) | 3.00 (0.00) |

*numbers in parenthesis are standard deviation of mean blink response for n = 6.

TTX-induced local anesthesia of de-epithelialized corneas varied as a function of dose. At 2 h after TTX application, all of the TTX concentrations showed some anesthetic effect. TTX at 1.0 mM, 0.1 mM, and 0.01 mM had mean anesthesia scores of 1.00 (SD=0.00, P=0.0011), 1.17 (SD=0.41, P=0.0076), and 1.50 (SD=0.84, P=0.0076) respectively. At 4 h, rabbit eyes that were treated with 1.0 mM and 0.1 mM TTX were still significantly anesthetic with mean anesthesia scores of 1.00 (SD=0.00, P=0.0011) and 1.67 (SD=0.52, P=0.0011), respectively. In contrast, the mean anesthesia score of rabbits treated with 0.01 mM TTX was returning to normal at 2.33 (SD=0.82) by 4 h. By 6 h, rabbit eyes treated with either 0.1 mM or 0.01 mM had mean scores of 2.83 (SD=0.41). At 6 h after TTX administration, five of six rabbit eyes treated with 1.0 mM TTX were still partially anesthetic with a mean anesthesia score of 1.50 (SD=0.84, P=0.0076). By 8 h the mean anesthesia score for 1.0 mM TTX was approaching normal at 2.50 (SD=0.84), with only two of six rabbits showing any anesthetic effect.

C. Dosing Frequency

Experiments were conducted to test whether TIX could produce prolonged effectiveness with repeated dosing. A 40 µl aliquot of 1 mM tetrodotoxin was administered every 6 hours for 24 hours to the centrally de-epithelialized cornea of 6 rabbits. Corneal sensation was monitored, by scoring the eye for blink response as described above, every 3 hours for 24 hours and at 17 hours, 30 hours and 34 hours after the initial dose. Response scores after administration of tetrodotoxin were compared to pre-operative response scores for statiscal analysis by the Wilcoxon test. The results are tabulated in Table 5 and shown in FIG. 4, where the arrows in the figure indicate the dosage times.

TABLE 5

| Time (hours) | Blink Response |
| --- | --- |
| 0 | 3.00 (0.00) |
| 3 | 1.00 (0.00) |
| 6 | 1.17 (0.41) |
| 9 | 1.00 (0.00) |
| 12 | 1.00 (0.00) |
| 15 | 1.00 (0.00) |
| 18 | 1.00 (0.00) |
| 21 | 1.17 (0.41) |
| 24 | 1.00 (0.00) |
| 17 | 1.00 (0.00) |
| 30 | 1.17 (0.41) |
| 34 | 2.83 (0.41) |

*numbers in parenthesis are standard deviation of mean blink response for n = 6.

At 3 hours after the first administration, all of the rabbit eyes were anesthetic with a mean anesthesia score of 1.00 (SD= 0.00, P=0.0011). All six rabbit eyes remained anesthetic for the duration of the experiment, with mean anesthesia scores ranging from 1.00 to 1.17 (P=0.0011 throughout). At 6 h after the final TTX administration and 30 h after the initial TTX administration, six of six rabbit eyes were still anesthetic with a mean anesthesia score of 1.17 (SD=0.41, P=0.0011). At 10 h after the final TTX administration and 34 h after the initial TTX administration, five of six rabbit eyes had normal sensation with a mean anesthesia score of 2.83 (SD=0.41).

Example 3

Administration of Tetrodotoxin to Partially De-epithelialized Rabbit Corneas

A. Corneal Abradement

To determine whether TTX inhibits corneal re-epithelialization, twelve New Zealand White rabbits were anesthetized with a mixture of keamine and xylazine. A corneal trephine was used to make Whatman #2 filter paper discs measuring 7.5 mm in diameter. The discs were soaked in n-heptanol solution and blotted to remove excess liquid. One disc was placed on the central cornea of the right eye of each rabbit for 30 seconds. After removal, the cornea was washed with balanced salt solution to remove the loosened epithelial cells. Topical fluorescein was applied and the diameter of the epithelial defect was measured in 2 meridians (12:00–6:00 and 3:00–9:00) using calipers. The radius of the defect was determined, and the defect area was calculated as previously described using an equation that corrects for the curvature of the rabbit cornea. Crosson C E, Klyce S D, Beuerman R W (1986) Epithelial wound closure in the rabbit cornea. Invest Ophthalmol Vis Sci 27:464–473.

B. Effect of Multiple Doses of TTX on Re-epithelialization of Abraded Rabbit Corneas The rabbits were randomized into two test groups for treatment with 40 µl of 1 mM tetrodotoxin every 8 hours or for no treatment. The rabbits were re-anesthetized with keratin and xylazine and epithelial defect size was re-measured with calipers at 17, 32, 42, 49, 56, and 66 h after the creation of epithelial defects. Twenty-four hours after the corneal epithelial defects were closed (completely healed), pachometry (Humphrey Ultrasonic Pachometer) was performed in both the experimental and fellow eyes of each rabbit.

Figure 5:
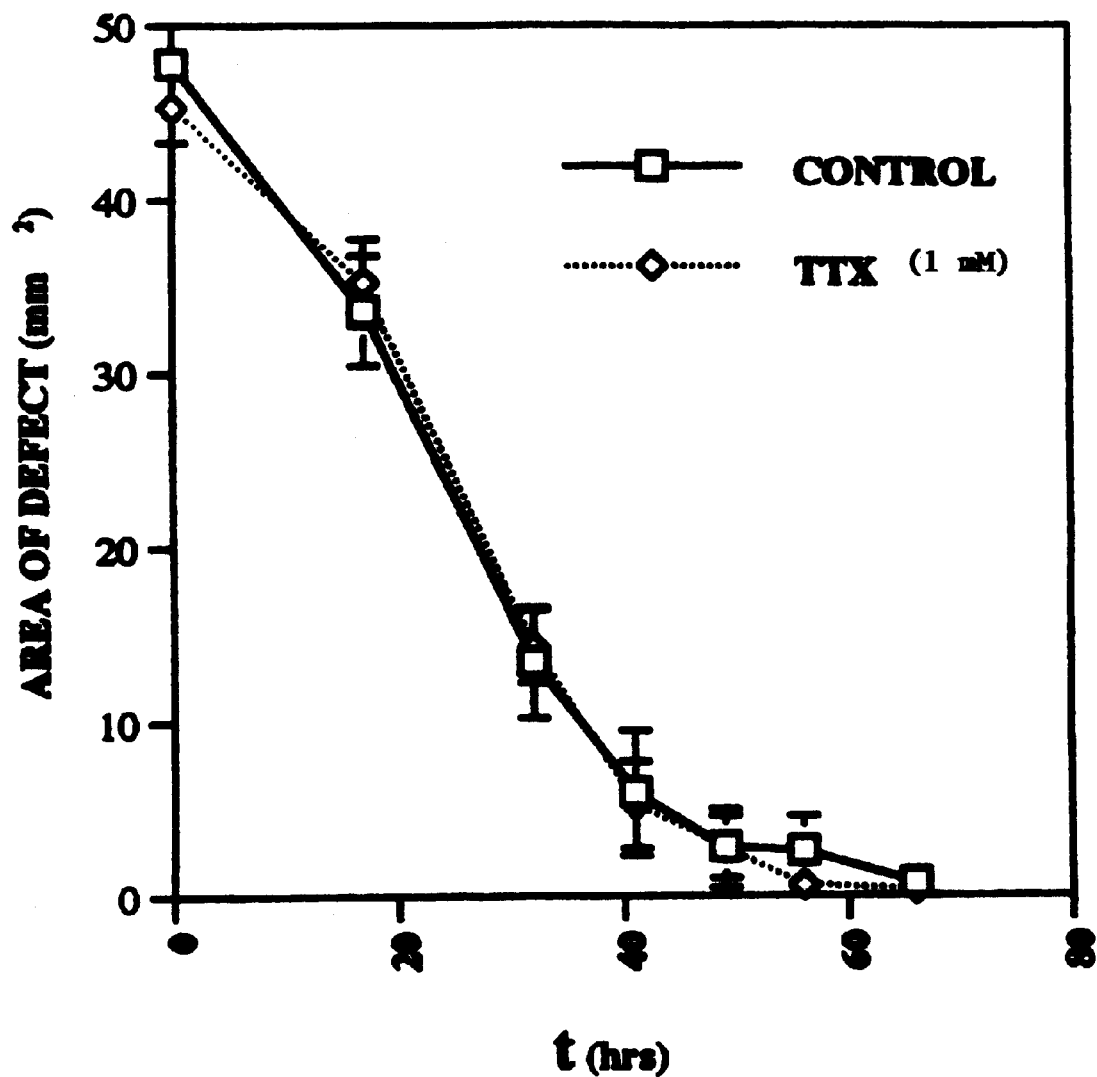

The results are shown in FIG. 5 and Table 6.

TABLE 6

| | Corneal Defect Size | |
| --- | --- | --- |
| | AREA 0F DEFECT (mm$^2$) | |
| TIME (h) | CONTROL | TTX |
| 0 | 53.0 +/− 2.0 | 49.0 +/− 5.8 |
| 17 | 35.6 +/− 8.9 | 37.9 +/− 7.1 |
| 32 | 12.9 +/− 6.4 | 15.7 +/− 7.1 |
| 42 | 5.7 +/− 9.5 | 5.6 +/− 6.3 |
| 49 | 2.8 +/− 4.4 | 3.0 +/− 5.7 |
| 56 | 2.7 +/− 5.1 | 2.5 +/− 5.9 |
| 66 | 0.7 +/− 1.6 | 0.3 +/− 0.7 |

Corneal defects of untreated and 1.0 mM TTX-treated corneas were essentially identical in their healing rates. By 48 h, four of six untreated corneas and three of six TTX-treated corneas were completely healed. At 56 h, four of six untreated and four of six TTX-treated corneas were completely healed. By 66 h, all but one cornea from each group had completely healed. In these remaining eyes, only a small defect, 0.67+/−1.63 mm2 for the TTX-treated rabbit and 0.29+/−0.72 mm2 for the untreated control rabbit, remained C. Effect of Multiple Doses of TTX on Corneal Thickness after Re-epithelialization In order to determine whether TTX had an effect on corneal thickness after re-epithelialization compared to untreated control eyes, corneal thickness was measured 92 hours after creation of a corneal abrasion (OD) in rabbit eyes that had been treated with multiple doses of 1.0 mM TTX. Corneal thickness of healed corneal abrasions (OD) and uninjured fellow eyes (OS) were measured by pachometry. The results are given as the mean defect area and the standard deviation (n=6)

TABLE 7

| DRUG TREATMENT | CORNEAL THICKNESS OD | OS |
| --- | --- | --- |
| NONE | 0.39 +/- 0.04 | 0.43 +/- 0.04 |
| 1.0 mM TTX | 0.40 +/- 0.04 | 0.41 +/- 0.05 |

There was no statistically significant difference in corneal thickness between untreated and TTX-treated corneas (Table 7).

Example 4

Topical Administration of Tetrodotoxin to Rabbit Eyes after Excimer Laser Keratectomy TTX in a pH 4.3 sodium citrate vehicle was used in the following experiments (Sigma Chemical Co., St. Louis, Mo.). New Zealand white rabbits were divided into two experimental groups, each consisting of six rabbits. After general anesthesia by intramuscular injection of a mixture of xylazine and keratin, followed by topical application of 0.5% proparacaine (Ophthetic, Allergan, Irvine, Calif.) to each right eye, the rabbits underwent excimer laser keratectomy on their right eyes.

Excimer laser keratectomy was performed using the Star Excimer Laser System (VISX, Inc.) in phototherapeutic keratectomy (PTK) mode. Excimer laser keratectomy was performed to create a 5 mm diameter wound, 75 $\mu$m in depth. The repetition rate of the laser was set at 6 Hz with a pulse energy density of 160 mJ/cm2.

One group of six rabbits then received a 40 $\mu$l aliquot of 1 mM TTX into the inferior conjunctival cul-de-sac of their right eyes and the other group of six rabbits received 40 $\mu$l of the pH 4.3 sodium citrate vehicle into the inferior conjunctival cul-de-sac of their right eyes as a control. The rabbits were treated with 1 mM TTX or vehicle again at 6, 12, 18, and 24 hours.

Corneal sensation was tested as previously described. Briefly, sensation was tested with a 5 mm silk suture mounted on a wooden cotton tip applicator. The cornea was stimulated with the suture in the mid-peripheral cornea, outside of the excimer laser keratectomy treated area. Care was taken not to stimulate the eyelashes. The rabbit's response was graded in the following fashion: no blink=1, partial blink without full eyelid closure=2, full blink=3. Corneal sensation was tested at 3, 6, 9, 12, 15, 18, 21, 24, 30, 32, and 40 hours. At 6, 12, 18 and 24 hours the corneal sensation was tested prior to re-administration of TTX or vehicle. The rabbits were observed for changes in feeding habits, movement, respiration and alertness. The data are presented in FIG. 6 as the mean score of 6 rabbits/treatment group. TTX treated eyes' anesthesia scores were compared to vehicle treated eyes' anesthesia scores for statistical significance by the Wilcoxon test.

Figure 6:
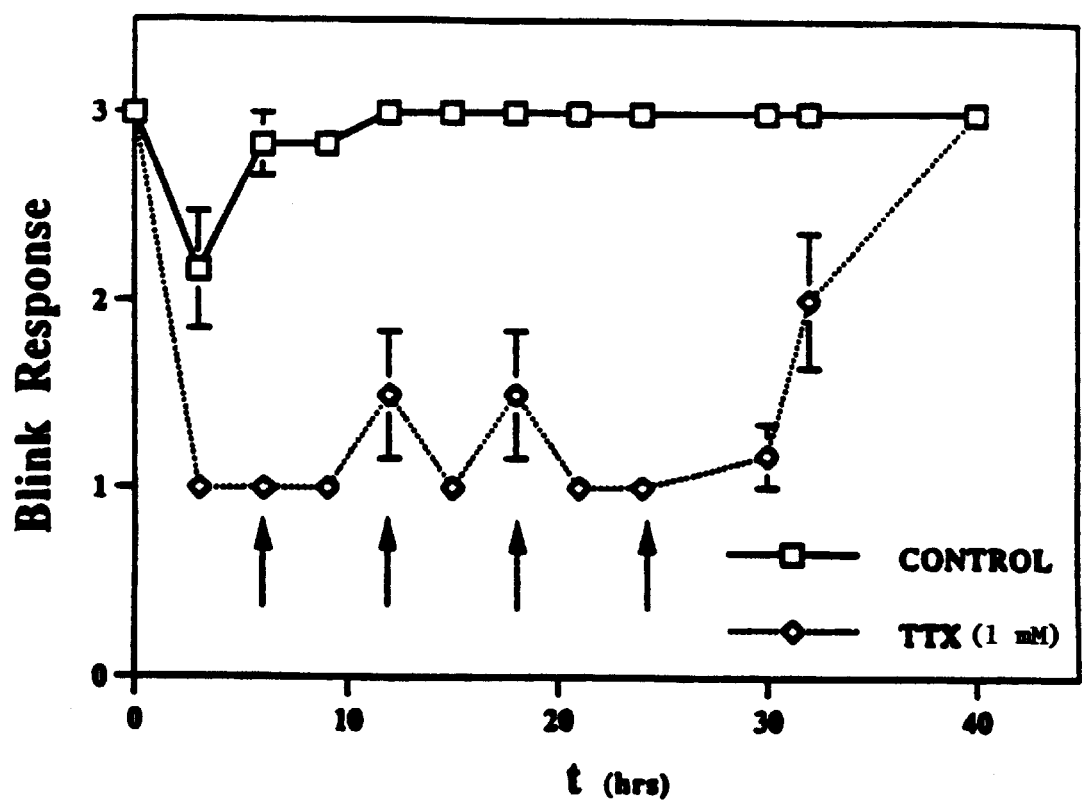

Administration of 40 $\mu$l of 1 mM TTX every 6 hours for 24 hours after excimer laser keratectomy produced nearly complete local anesthesia for at least 30 hours with a mean anesthesia score of 1.17 (SD=0.41) (p=0.011, Wilcoxon test) (FIG. 6). Three hours following each application of TTX, the mean anesthesia score for TTX treated eyes was 1.0 (SD=0). Six hours following each application of TTX the mean anesthesia scores were between 1.0 (SD=0) and 1.5 (SD=0.84). At least 4/6 of the rabbits were completely anesthetic at six hours following each application of TTX. At 32 hours, 8 hours following the final application of TTX, there was still significant local anesthesia of the TTX treated corneas (p=0.0325, Wilcoxon test). The mean anesthesia score was 2.0 (SD=0.89). At 40 hours, 18 hours following the final application of TTX, all of the rabbits' corneas had returned to normal sensation. In contrast, after 9 hours, vehicle treated eyes all had normal sensation for the duration of the experiment (FIG. 6). There was a very slight local anesthesia of the vehicle treated eyes at 6 and 9 hours following excimer laser keratectomy, with the mean anesthesia score being 2.83 (SD=0.41). However, this was due in each case to 1/6 rabbits scoring 2, 5/6 rabbits scoring 3, and was not significant. At 3 hours following excimer laser keratectomy the vehicle treated eye's mean anesthesia score was 2.16 (SD=0.75). This was probably due to lingering effects of the general and topical anesthetics that were administered prior to the excimer laser keratectomy procedure.

Example 5

Effect of Topical Administration of TTX Following PRK on Corneal Re-epithelialization To determine whether TTX inhibited corneal re-epithelialization following excimer laser keratectomy, topical fluorescein was applied after rabbits were given general anesthesia by intramuscular injection of a mixture of xylazine and keratin. The diameter of the circular epithelial defect was measured using calipers in 2 meridians (12:00–6:00 and 3:00–9:00), and the radius of the defect was calculated. The radius was used to calculate the area of the defect using the method of Crosson et al. that corrects for the curvature of the rabbit cornea (Crosson C E, et al., Invest Ophthalmol Vis Sci., 27:464–473 (1986)). General anesthesia was administered and the size of the epithelial defect was measured at 24, 40, 49, 63, 68, and 72 hours following excimer laser keratectomy. Observers were masked as to the contents of eye drops given to the rabbits.

To assess whether or not repeated administration of TTX had any effect on the rate of epithelial healing, epithelial defect area was measured over 72 hours following excimer laser keratectomy. As shown in FIG. 7, there was little difference in healing rate of vehicle and TTX treated eyes. At 24 hours there was no significant difference in healing between TTX treated and vehicle treated eyes (p>0.05, t-test). At 40 hours the TTX treated eyes had larger defects than vehicle treated eyes 7.85 mm2 vs. 4.54 mm2 (p<0.025, t-test). However, at 49 hours, and thereafter, both groups were equally healed (p>0.05, t-test).

Toxicity.

The rabbits involved in the corneal anesthesia and corneal wound healing experiments following excimer laser keratectomy described above were observed carefully for any signs of systemic toxicity during the course of the experiment. No rabbit had any alterations of feeding, movement, respiration, or alertness during this period that suggested a toxic effect of the TTX. No rabbit died or was noted to have abnormalities in behavior subsequent to TTX administration. Additionally, no signs of local toxicity such as ocular injection or corneal haze were apparent in any rabbit.

Example 6

Systemic Absorption of TTX Topically Applied to Abraded Rabbit Eyes

TTX (Alexis Corporation) was formulated into 20 $\mu$l doses containing 100 $\mu$g of m in a pH 4.3 citrate buffer (60 mM). Four Dutch banded rabbits were weighed. After general anesthesia by intramuscular injection of a mixture of xylazine and keratin, followed by topical application of 0.5% proparacaine to each eye, a #69 Beaver blade was used to create a central epithelial defect which measured between 4 mm diameter in one eye of each rabbit. Each rabbit then received a 20 μl aliquot of TTX into the inferior conjunctival cul-de-sac of the abraded eye. At 10 min, 20 min and 40 min following administration of TTX, 4 ml of blood was taken from each rabbit. The blood was clotted and the serum collected.

TTX was purified from serum samples using the purification scheme of Yasumoto and Michishita. Fluorometric determination of tetrodotoxin by high performance liquid chromatography. Agric Biol Chem 49: 3077–3080 (1985). Briefly, 300 μl of each serum sample was extracted by boiling for 10 min in 0.02N acetic acid, and TTX was purified by chromatography over Amberlite CG-50. TTX was eluted from the Amberlite with 0.5 N acetic acid, samples were dried in a vacuum centrifuge and TTX was resuspended in 50 μl of phosphate buffered saline.

Figure 9:
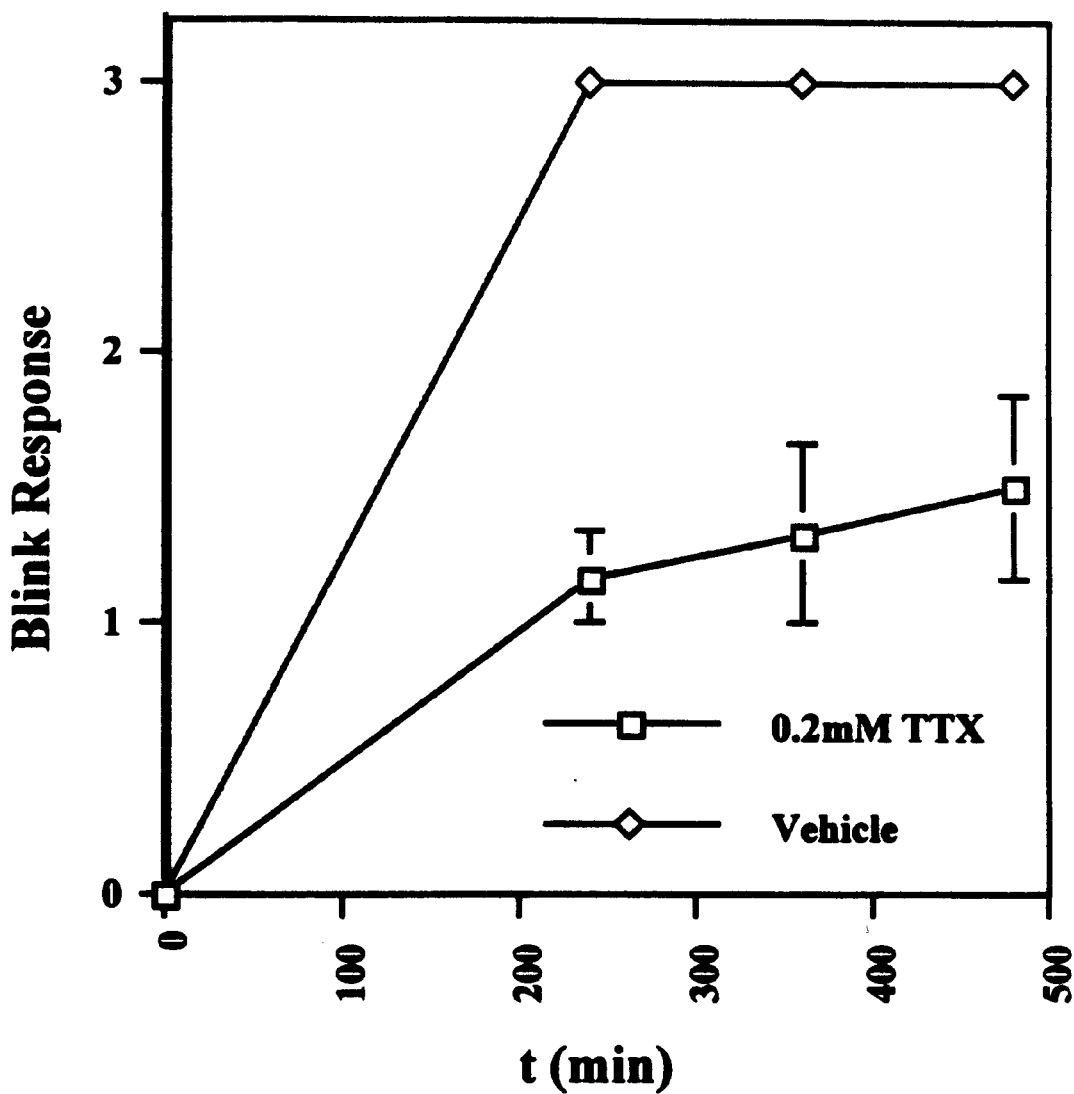
Figure 10:
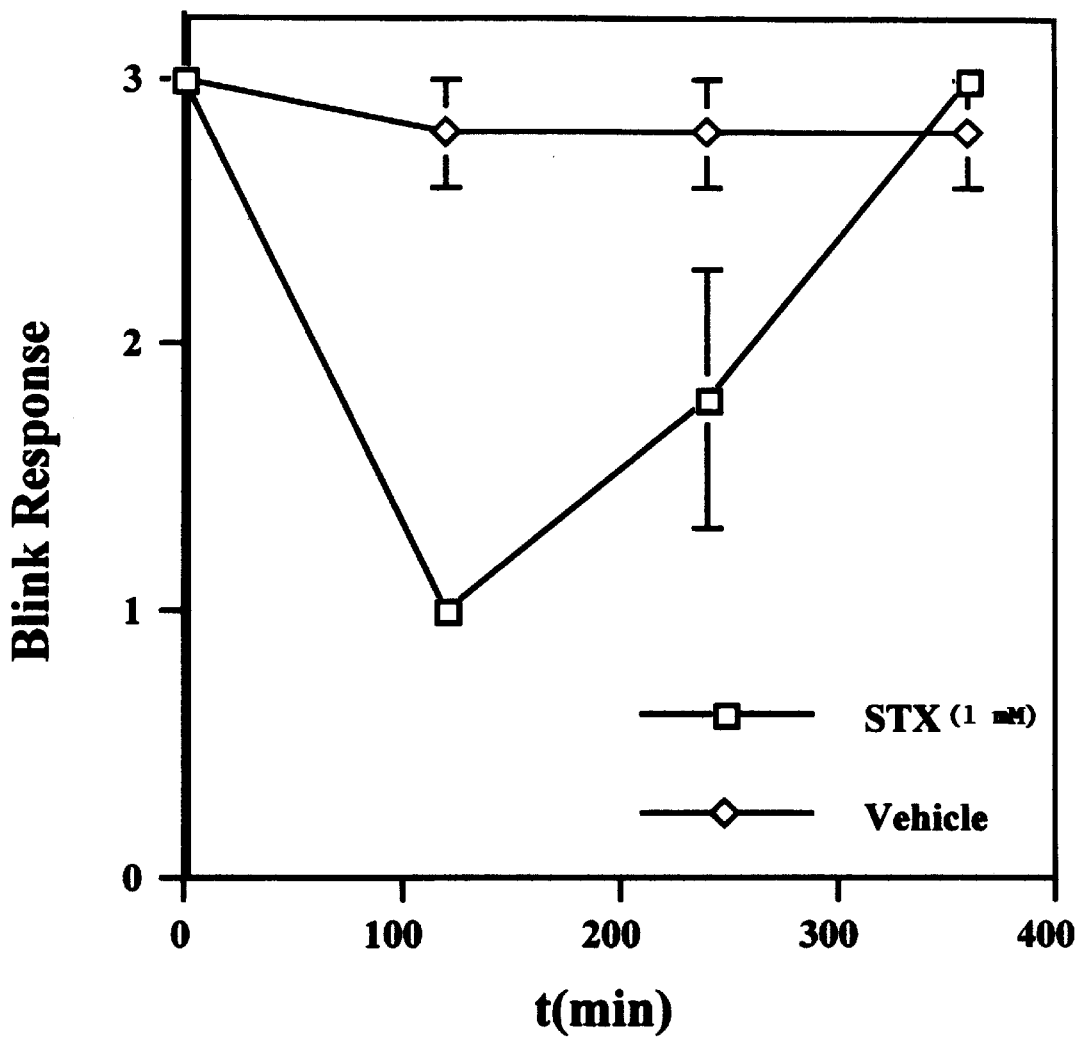

Assays to quantify the amount of TTX purified from serum samples were performed using a tissue culture bioassay. Hamasaki, K, Kogure, K and Ohwada, K. A biological method for the quantitative measurement of tetrodotoxin (TTX): tissue culture bioassay in combination with a water-soluble tetrazolium salt. Toxicon 34: 490–495 (1996). Briefly, 2 to 3×10⁵ mouse Neuro 2A cells per well were plated on 96 well microtiter plates in 200 μl of RPMI-1640 medium containing 10 fetal bovine serum and incubated overnight in a 37° C. tissue culture incubator. After 24 hours the cells were given 10 μl of the TTX samples, 20 μl of 10 mM ouabain, and 20 μl of 0.5 mM veratridine. After an additional 24 hours at 37° C., the cells were given 20 μl of WST-1 cell counting reagent (Dojindo Corp.) and allowed to incubate an additional 3 hours at 37° C. The yellow color produced by the WST-1 reagent was quantified by reading the absorbance at 430 nm with a reference wave length of 600 nm. All assays were performed in duplicate. TTX concentrations were derived by comparison to a standard curve generated using normal rabbit serum that had been spiked with known amounts of pure TTX and subjected to the same purification scheme as the rabbit serum samples. The results are given in Table 8 as the average amount of TTX in $\mu$g per ml of serum at each time point in the table +/− standard deviation (N=4) (SE=Standard Error). The average amount of TTX absorbed into the serum is derived by assuming a serum volume equal to 3% of the mass of each rabbit. Kaplan, H M and Timmons, E H. The Rabbit: a Model of the Principals of Mammalian Physiology and Surgery. Academic Press, NY (1979).

TABLE 8

| Time (mins) | TTX ($\mu$g/ml) | Std. Error | TTX in Serum (Total $\mu$g absorbed) | Std. Error |
|---|---|---|---|---|
| 0 | 0 | | 0 | |
| 10 | 0.16 +/− 0.09 | (SE = 0.04) | 6.39 +/− 4.61 | (SE = 2.30) |
| 20 | 0.33 +/− 0.16 | (SE = 0.08) | 14.44 +/− 6.09 | (SE = 3.04) |
| 40 | 0.31 +/− 0.11 | (SE = 0.06) | 13.92 +/− 4.06 | (SE = 2.03) |

Thus, after 20 minutes about 14% of the applied dose of TTX was absorbed into the serum. This persisted for at least 40 minutes.

Example 7

Topical Application of Single Dose (20 $\mu$l) of 0.1 mM TTX to Abraded Rabbit Cornea TTX (Alexis Corporation) was obtained and formulated into a 0.1 mM concentration in a pH 4.3 sodium citrate vehicle (60 mM). Dutch banded rabbits were divided into two experimental groups of five and six. After general anesthesia by intramuscular injection of a mixture of xylazine and keratin, followed by topical application of 0.5% proparacaine to each eye, a #69 Beaver blade was used to create a central epithelial defect which measured between 4 mm diameter in both eyes of each rabbit. Five rabbits received a 20 $\mu$l aliquot of 0.1 mM TTX into one eye and six rabbits received 20 $\mu$l of the pH 4.3 sodium citrate vehicle as a control into one eye. Experimenters were masked to the contents of each aliquot.

Corneal sensation was tested with a 4-0 silk suture mounted upon a wooden cotton tip applicator such that the suture extended 5 mm beyond the wooden end of the applicator. Because the central cornea was often rendered anesthetic following mechanical epithelial debridement, the cornea was stimulated in the mid-peripheral cornea, outside of the abraded area, with the suture to produce grossly visible indentation of the cornea as the endpoint. Care was taken not to stimulate the eyelashes. The rabbit's response was graded in the following fashion; no blink=1, partial blink without full eyelid closure=2, full blink=3. A score of 3 indicates full responsiveness and a score of 1 indicates full local anesthesia. Corneal sensation was tested prior to administration of drugs and again at 4 and 6 hours. The rabbits were observed for changes in feeding habits, movement, respiration and alertness for 24 hours. The data are presented as the mean score of 6 rabbits/treatment group. TTX treated eyes' anesthesia scores were compared to their vehicle treated fellow eyes' anesthesia scores for statistical analysis by the Wilcoxon test. The results are shown in FIG. 8.

At 4 hours the vehicle treated eyes had an average anesthesia score of 2.67 (SD=0.52). In contrast the TTX treated eyes were significantly anesthetic with a mean score of 1.20 (SD=0.45) (p=0.0411). At 6 hours the vehicle treated eyes had a mean anesthesia score of 3.00 (SD=0.00). In contrast at 6 hours the TTX treated eyes were still significantly anesthetic with a mean anesthesia score of 2.00 (SD=1.00) (p=0.0411). Thus, one 20 $\mu$l dose of 0.1 mM TTX provided at least 6 hours of local anesthesia when applied to an abraded rabbit cornea.

Example 8

Topical Application of Single Dose (20 $\mu$l) of 0.2 mM TTX to Abraded Rabbit Cornea TTX was obtained and formulated into a 0.2 mM concentration in a pH 4.3 sodium citrate vehicle (60 mM). Dutch banded rabbits were divided into two experimental groups of five and six. After general anesthesia by intramuscular injection of a mixture of xylazine and keratin, followed by topical application of 0.5% proparacaine to each eye, a #69 Beaver blade was used to create a central epithelial defect which measured between 4 mm diameter in both eyes of each rabbit. Six rabbits received a 20 $\mu$l aliquot of 0.2 mM TTX into one eye and five rabbits received 20 $\mu$l of the pH 4.3 sodium citrate vehicle as a control into one eye. Experimenters were masked to the contents of each aliquot.

Corneal sensation was tested with a 4-0 silk suture mounted upon a wooden cotton tip applicator such that the suture extended 5 mm beyond the wooden end of the applicator. Because the central cornea was often rendered anesthetic following mechanical epithelial debridement, the cornea was stimulated in the mid-peripheral cornea, outside of the abraded area, with the suture to produce grossly visible indentation of the cornea as the endpoint. Care was taken not to stimulate the eyelashes. The rabbit's response was graded in the following fashion; no blink=1, partial blink without full eyelid closure=2, full blink=3. A score of 3 indicates full responsiveness and a score of 1 indicates full anesthesia. Corneal sensation was tested prior to administration of drugs and again at 4, 6, and 8 hours. The rabbits were observed for changes in feeding habits, movement, respiration and alertness for 24 hours. The data are presented as the mean score of 6 rabbits/treatment group. TTX treated eyes' anesthesia scores were compared to their vehicle treated fellow eyes' anesthesia scores for statistical analysis by the Wilcoxon test. The results are shown in FIG. 9

All of the vehicle treated eyes were normal throughout the experimental period with an average anesthsia score of 3.00 (SD=0.00). In contrast the TTX treated eyes showed significant local anesthesia. At 4 hours the TTX treated eyes were significantly anesthetic with a mean score of 1.17 (SD=0.41) (p=0.0022). At 6 hours the TTX treated eyes were still significantly anesthetic with a mean anesthesia score of 1.33 (SD=0.82) (p<0.0152). At 8 hours the TTX treated eyes were still significantly anesthetic with a mean anesthesia score of 1.50 (SD=0.84) (p<0.0152). Thus, one 20 $\mu$l dose of 0.2 mM TTX provided at least 8 hours of local anesthesia when applied to an abraded rabbit cornea.

Example 9

Calculation of Dosages

TTX has been determined to be an effective and non-toxic anesthetic for topical administration to partially de-epithelialized rabbit corneas for at least 6 h at a dose of 1.0 mM, or approximately 1.0–1.8% of the estimated lethal human dose. Even lower effective dosages for topical administration to partially de-epithelialized rabbit corneas were established, including 20 μl aliquots of either 0.1 mM TTX or 0.2 mM TTX, corresponding to 0.6 μg and 1.27 μg, respectively.

While the toxic dose of TTX has been well studied in a number of animal species (Kao CY, Tetrodotoxin, saxitoxin and their significance in the study of excitation phenomena. Pharm Rev 18:997–1049 (1966)), it has been only imprecisely estimated for humans. Cornish reported a case of TTX intoxication and estimated the lethal oral dose to be about 10–18 μg/kg based on the amount of fish tissue consumed (Cornish J N, Susceptibility of man to pufferfish toxin. Med J Aust 2:48 (1973)). For a 70-kg person, the lethal dose would therefore be 0.7–1.26 mg. The dose lethality curve for TTX is very steep. In mice, the minimum intraperitoneal lethal dose is 8 μg/kg and the LD100 is 12 μg/kg (Kao CY, Fuhrman F A, Pharmacological studies on tarichatoxin, a potent neurotoxin. J Pharmacol 140:31–40 (1963)). The lethal dose for oral administration in mice is much higher, 332 μg/kg (Kao CY, Pharm Rev 18:997–1049 (1966)). Because of the steep dose-lethality curve, reduction of the effective topical dose of TTX to 1% or less of the minimum lethal dose should result in a therapeutically useful dose.

More sensitive testing systems using an esthesiometer, such as the Boberg-Ans or the Cochet and Bonnet device are well-known in the field and can be used to determine safe human dosages. Such testing can help determine whether TTX can produce partial local anesthesia or analgesia at doses even lower than 1.0–1.8% of the estimated lethal human dose used in this study.

Example 10

Topical Administration of Saxitoxin (STX) to Partially De-epithelialized Rabbit Corneas Saxitoxin (Alexis Corporation) was formulated into 1 mM concentration in balanced saline solution (BSS). Ten Dutch banded rabbits were divided into two experimental groups of five. After general anesthesia by intramuscular injection of a mixture of xylazine and keratin, followed by topical application of 0.5% proparacaine to each eye, a #69 Beaver blade was used to create a central epithelial defect which measured between 4 mm diameter in one eye of each rabbit. Five rabbits then received a 20 μl aliquot of Saxitoxin into the inferior conjunctival cul-de-sac of one eye and five rabbits received a 20 μl aliquot of the BSS vehicle as a control into the fellow eye. Experimenters were masked to the contents of each aliquot.

Corneal sensation was tested with a 4-0 silk suture mounted upon a wooden cotton tip applicator such that the suture extended 5 mm beyond the wooden end of the applicator. Because the central cornea was often rendered anesthetic following mechanical epithelial debridement, the cornea was stimulated in the mid-peripheral cornea, outside of the abraded area, with the suture to produce grossly visible indentation of the cornea as the endpoint. Care was taken not to stimulate the eyelashes. The rabbit's response was graded in the following fashion; no blink=1, partial blink without full eyelid closure=2, full blink=3. A score of 3 indicates full responsiveness and a score of 1 indicates full local anesthesia. Corneal sensation was tested prior to administration of drugs and again at, 2, 4, and 6 hours. The rabbits were observed for changes in feeding habits, movement, respiration and alertness for 24 hours. The data are presented as the mean score of 5 rabbits/treatment group. The results are shown in FIG. 10 (As the mean local anesthesia score +/− standard error) and again in Table 9 (as the mean anesthesia score +/− the standard deviation). Statistical analysis was by the Wilcoxon test.

TABLE 9

| Time (min) | 1 mM Saxitoxin | Vehicle |
|---|---|---|
| 120 | 1.0 +/− 0.00 | 2.8 +/− 0.45 |
| 240 | 1.80 +/− 1.09 | 2.8 +/− 0.45 |
| 360 | 3.0 +/− 0.00 | 2.8 +/− 0.45 |

After 2 hours all of the Saxitoxin treated rabbit eyes were significantly anesthetic compared to vehicle treated eyes with a mean anesthesia score of 1.0 (SD=90)(p=0.004). In contrast the vehicle treated eyes had an mean anesthesia score of 2.8 (SD=0.45). After 4 hours the Saxitoxin treated eyes were still significantly anesthetic with a mean anesthesia score of 1.8 (SD=1.09)(p=0.0159), while the vehicle treated eyes had a mean anesthesia score of 2.8 (SD=0.45). By 6 hours the Saxitoxin treated eyes had returned to normal with a mean anesthesia score of 3.0 (SD=0), while the vehicle treated eyes had a mean anesthesia score of 2.8 (SD=0.45). None of the rabbits showed any signs of systemic toxicity. Thus, treatment of corneal abraded rabbit corneas with 20 μl of 1 mM Saxitoxin provided at least 4 hours of corneal anesthesia.

References

Blakenship, J. E., *Perspectives in Biology and Medicine*, summer:509–526 (1976).

Bower, D. J., et al., *Clinical Toxicology*, 18(7), 813–863 (1981).

Cherry, P. M., et al., *Supplement to Ophthalmic Surgery and Lasers*, 25(5), S477–80 (1996).

Clayman, C. B., "THE AMERICAN MEDICAL ASSOCIATION ENCYCLOPEDIA OF MEDICINE", Random House, New York, (1989).

Goto, T. et al., Tetrodotoxin, Tetrahedron, 21:2–59–2088 (1965).

Hamasaki K. et al., A Biological Method for the Quantitative Measurement of Tetrodotoxin (TTX): Tissue Culture Bioassay in Combination with a Water-Soluble Tetrazolium Salt, Toxicon. 34(4):490–495 (1996).

Lee, V. and Robinson, J. R., Review: Topical Ocular Drug Delivery: Recent Developments and Future Challenges, J. Ocular Pharmacol. 2(1):67–108 (1986).

Kao, C. Y., *Pharmaceutical Reviews*, 18(2), 997–1049 (1966).

Ogura, Y. and Mori, Y., *European Journal of Pharmacology*, 3:58–67 (1968).

Salminen L., Review: Systemic Absorption of Topically Applied Ocular Drugs in Humans, J. Ocular Pharmacol., 6(3):243–249 (1990).

Schwartz, D. M. et al., Experimental Use of Tetrodotoxin for Corneal Pain After Excimer Laser Keratectomy, Cornea 17(2):196–199 (1998).

Tutton M. K., et al., *J. Cataract Refract Surg.* 22(5), 536–541 (1996).

Rosenberg, G. J. et al., *Clinics in Plastic Surgery*, 23(1):29 (1996).

Rosenwasser, G. O. D., *Intl. Ophthalmology Clinics*, 29(3), 153–158 (1989).

All publications and patent applications mentioned in this specification are herein incorporated by reference to the same extent as if each individual publication or patent application was specifically and individually indicated to be incorporated by reference.

Although the invention has been described with respect to particular embodiments, it will be apparent to one of ordinary skill in the art that many changes and modifications can be made thereto without departing from the spirit or scope of the invention.

We claim:

1. A method of producing local anesthesia in a partially or completely de-epithelialized tissue region of a mammal, comprising topically administering an anesthetically effective dose of a pharmaceutical composition consisting essentially of a long-acting sodium channel blocking compound, in a pharmaceutically suitable vehicle, to said de-epithelialized tissue region of said mammal, wherein said de-epithelialized tissue region is a corneal region, a region in the upper or lower gastrointestinal tract, or a genital lesion in the genital area.

2. The method of claim 1, wherein said long-acting sodium channel blocking compound does not inhibit re-epithelialization of said epithelial tissue region.

3. The method of claim 2, wherein said sodium channel blocking compound is administered every 6–8 hours for between about 24–72 hours.

4. The method of claim 2, wherein said long-acting sodium channel blocking compound is a compound capable of specifically binding to a site on an extracellular region of a sodium channel alpha subunit.

5. The method of claim 4, wherein said site is on an SS2 extracellular region of a sodium channel alpha subunit.

6. The method of claim 5, wherein said long-acting sodium channel blocking compound is tetrodotoxin.

7. The method of claim 6, wherein said effective dose of tetrodotoxin is administered from a formulation containing tetrodotoxin at a concentration of between 0.001–10 mM.

8. The method of claim 6, wherein said tetrodotoxin is administered in a vehicle having a pH of between 4–8.

9. The method of claim 8, wherein said vehicle has a pH of between 5–7.5.

10. The method of claim 5, wherein said long-acting sodium channel blocking compound is saxitoxin.

11. The method of claim 1, wherein said administering is to a partially or completely de-epithelialized comeal tissue region.

12. The method of claim 1, wherein said administering comprises instilling drops of said sodium channel blocking compound to the eye following corneal surgery.

13. The method of claim 1, wherein said epithelial tissue region is a region in the upper or lower gastrointestinal tract.

14. The method of claim 1, wherein said epithelial tissue region is associated with genital lesions in the genital area.

15. A method of producing local anesthesia in an eye of a mammal, comprising topically administering to the corneal surface of the eye of said mammal, in an ophthalmically suitable vehicle, an anesthetically effective dose of a pharmaceutical composition consisting essentially of a long-acting sodium channel blocking compound, said corneal surface having an epithelial layer that is partially or completely de-epithelialized.

16. The method of claim 15, wherein said long-acting sodium channel blocking compound is a compound capable of specifically binding to a site on an extracellular region of a sodium channel alpha subunit, wherein said site is on either an SS1 region or an SS2 region.

17. The method of claim 16, wherein said long-acting sodium channel blocking compound is tetrodotoxin and said effective dose is administered from a formulation containing tetrodotoxin at a concentration between about 0.001–10 mM.

18. The method of claim 17, wherein said long-acting sodium channel blocking compound is tetrodotoxin and said effective dose is administered from a formulation containing tetrodotoxin at a concentration between about 0.01 mM to 0.2 mnM.

19. The method of claim 18, wherein said tetrodotoxin is administered in a vehicle having a pH of between about 4–8.

20. A method of reducing pain in a mammal following corneal refractive surgery, comprising, topically administering to a partially or completely de-epithelialized corneal surface of an eye of said mammal, in an ophthalmically suitable vehicle, a pain reducing effective dose of a pharmaceutical composition consisting essentially of a long-acting sodium channel blocking compound.

21. The method of claim 20, further comprising the step of instilling drops of a non-steroidal anti-inflammatory compound in the eye of said mammal.

22. The method of claim 20, further comprising administering to said mammal an antibiotic or a non-steroidal anti-inflammatory drug.

23. A method of reducing pain in a mammal following corneal refractive surgery, comprising topically administering to a corneal surface of an eye of said mammal, in an ophthalmically suitable vehicle, a pain reducing effective dose of a pharmaceutical composition consisting essentially of a long-acting sodium channel blocking compound, wherein said administering is by applying to the eye of said mammal a bandage contact lens, wherein said lens is capable of delivering said long-acting sodium channel blocking compound to said corneal surface.

24. As an article of manufacture, an ophthalmically acceptable dosage container comprising:

(a) a pharmaceutical composition consisting essentially of from about 0.003 μg to 160 μg of tetrodotoxin in an ophthalmically acceptable vehicle at pH of between about 4–8.

25. The article of claim 24, wherein said container comprises: from about 0.127 μg to 2.54 μg of tetrodotoxin.

26. A local anesthetic composition which consists essentially of an anesthetically effective amount of tetrodotoxin, in a concentration of 0.01 mM to 1 mM, in an ophthalmically acceptable vehicle at pH 4–6.

27. The composition of claim 26, wherein said concentration is between 0.01 mM and 0.2 mM tetrodotoxin.

28. The composition of claim 26, wherein said concentration is between 0.01 mM and 0.1 mM tetrodotoxin.

29. A local anesthetic composition which consists essentially of an anesthetically effective amount of saxitoxin, in a concentration of 0.1 mM to 10 mM, in an ophthalmically acceptable vehicle at pH 4–8.

30. A local anesthetic composition which consists essentially of an anesthetically effective amount of tetrodotoxin, in a concentration of 0.1 mM to 10 mM, in an ophthalmically acceptable vehicle at pH 4–6.

31. A method of producing a non-toxic local anesthesia in an epithelial tissue region of a mammal, comprising topically administering an anesthetically effective dose of a pharmaceutical composition consisting essentially of a long-acting sodium channel blocking compound, in a pharmaceutically suitable vehicle comprising a citrate buffer at pH 4–8, to said epithelial tissue region of said mammal.

32. The method of claim 31, wherein said pH is 4–5.

33. The method of claim 31, wherein said anesthesia has a duration of 4–8 hours.

34. The method of claim 31, wherein said long-acting sodium channel blocking compound does not inhibit re-epithelialization of said epithelial tissue.

35. A non-toxic local anesthetic composition which consists essentially of an anesthetically effective amount of tetrodotoxin, in a concentration of 0.01 mM to 10 mM, in an ophtalmically acceptable vehicle comprising citrate buffer at pH 4–8.

36. The composition of claim 35, wherein said pH is 4–5.

37. The composition of claim 35, wherein said pH is 4–5.

38. A non-toxic local anesthetic composition which consists essentially of an anesthetically effective amount of saxitoxin, in a concentration of 0.01 mM to 10 mM, in an ophtalmically acceptable vehicle comprising citrate buffer at pH 4–8.

* * * * *